United States Patent
Yokoi et al.

(10) Patent No.: US 8,658,107 B2
(45) Date of Patent: Feb. 25, 2014

(54) ISOLATOR

(75) Inventors: Yasuhiko Yokoi, Moriguchi (JP); Jiro Ohnishi, Moriguchi (JP); Akifumi Iwama, Moriguchi (JP); Masaki Harada, Moriguchi (JP); Yoshiaki Noguchi, Moriguchi (JP)

(73) Assignee: Panasonic Healthcare Co., Ltd., Toon-shi, Ehime (JP)

( * ) Notice: Subject to any disclaimer, the term of this patent is extended or adjusted under 35 U.S.C. 154(b) by 772 days.

(21) Appl. No.: 12/863,080

(22) PCT Filed: Aug. 20, 2009

(86) PCT No.: PCT/JP2009/003981
§ 371 (c)(1),
(2), (4) Date: Jul. 15, 2010

(87) PCT Pub. No.: WO2010/021139
PCT Pub. Date: Feb. 25, 2010

(65) Prior Publication Data
US 2011/0058986 A1 Mar. 10, 2011

(30) Foreign Application Priority Data
Aug. 20, 2008 (JP) ................... 2008-212233
Sep. 22, 2008 (JP) ................... 2008-243258

(51) Int. Cl.
*A61L 2/00* (2006.01)
*B01D 47/00* (2006.01)
*B01L 1/04* (2006.01)

(52) U.S. Cl.
USPC ........... 422/298; 422/292; 422/305; 422/306; 96/227; 96/243; 96/417; 96/424; 454/187; 454/228

(58) Field of Classification Search
USPC ............. 422/3, 5, 28, 105, 119, 292, 298, 422/305–306; 96/121, 227, 243, 397, 417, 96/424; 454/187, 228
See application file for complete search history.

(56) References Cited

U.S. PATENT DOCUMENTS
7,578,973 B2 * 8/2009 Call et al. .................. 422/83

FOREIGN PATENT DOCUMENTS
EP  1 707 221 A1  10/2006
JP  62-67418 A  3/1987
(Continued)

OTHER PUBLICATIONS

Japanese Patent Office machine English translation of the Detailed Description section of JP 2006-068122.*

(Continued)

*Primary Examiner* — Monzer R Chorbaji
(74) *Attorney, Agent, or Firm* — Westerman, Hattori, Daniels & Adrain, LLP

(57) ABSTRACT

An isolator includes a work chamber, a sterilizing substance supply unit, a gas flow channel pressure adjustment unit, a work chamber barometer, and a controller. The controller is configured to control execution of a gas flow channel leak test for checking a gas leak in a gas flow channel based on a detection result by the work chamber barometer after making the gas flow channel pressure adjustment unit increase or decrease the pressure in the gas flow channel, and is configured to control supply of the sterilizing substance by the sterilizing substance supply unit. The controller performs heating of a heater, which accompanies the supply of the sterilizing substance, in parallel with the gas flow channel leak test.

27 Claims, 13 Drawing Sheets

(56) References Cited

FOREIGN PATENT DOCUMENTS

| | | | |
|---|---|---|---|
| JP | 1-268557 A | 10/1989 | |
| JP | 2005-218548 A | 8/2005 | |
| JP | 2005-312799 A | 11/2005 | |
| JP | 2006-068122 * | 3/2006 | ............... A61L 2/20 |
| JP | 2006-68122 A | 3/2006 | |
| JP | 2007-105597 A | 4/2007 | |
| JP | 2007-202628 A | 8/2007 | |
| JP | 2008-68088 A | 3/2008 | |
| JP | 2008-145337 A | 6/2008 | |

OTHER PUBLICATIONS

Extended European Search Report dated Aug. 7, 2012, issued in corresponding European Patent Application No. 09808075.7, (11 pages).

International Preliminary Report on Patentability ( Forms PCT/IB/373) of International Application No. PCT/JP2009/003981 issued date Mar. 8, 2011 with Form PCT/ISA/237.

International Search Report of PCT/JP2009/003981, date of mailing Sep. 29, 2009.

* cited by examiner

ISOLATOR

CROSS-REFERENCE TO RELATED APPLICATIONS

This application is a National Stage of PCT/JP2009/003981, filed on Aug. 20, 2009 and claims the benefit thereof, which is based upon and claims the benefit of priority of Japanese Patent Application No. 2008-212233 filed on Aug. 20, 2008 and Japanese Patent Application No. 2008-243258 filed on Sep. 22, 2008. The entire contents of which are incorporated herein by reference.

FIELD OF THE INVENTION

The present invention relates to an isolator.

DESCRIPTION OF THE RELATED ART

An isolator includes therein a work chamber that is under a sterile environment and is used for the work that is performed in a sterile environment in the work chamber, for example, for a work in which a biomaterial is handled, such as cell culture. Herein, the sterile environment means an environment that is as close to a dust-free, sterile environment as possible to prevent contamination of substances other than ones necessary for the work to be performed in the work chamber.

In an isolator, to maintain the sterile environment in the work chamber, a sterilizing process is performed in which a sterilizing substance, such as hydrogen peroxide, is supplied into the work chamber such that the inside of the work chamber is sterilized (see Japanese Patent Application Publications Nos. 2006-68122 and 2005-218548). In the isolator system described in Japanese Patent Application Publication No. 2006-68122, liquid hydrogen peroxide is vaporized by being hit with dried, hot air and the resultant hydrogen peroxide gas is supplied into the isolator. In the decontamination apparatus described in Japanese Patent Application Publication No. 2005-218548, hydrogen peroxide solution is vaporized by a heater and the resultant hydrogen peroxide gas is supplied into the isolator.

If a large amount of a sterilizing substance leaks out from the sterilized space, including a work chamber, during a sterilizing process, the concentration of the sterilizing substance is decreased, thereby possibly leading to insufficient sterilization. In addition, because a sterilizing substance, such as hydrogen peroxide, is harmful to human bodies, it is desirable that the sterilizing substance does not leak out from an isolator. Accordingly, in the decontamination apparatus described in Japanese Patent Application Publication No. 2005-218548, a leak test of the isolator is performed prior to the supply of the sterilizing substance.

Also, in an isolator, the air that has been taken in from a gas supply unit is supplied into the work chamber through a particulate trap filter, such as HEPA filter (High Efficiency Particulate Air filter), which is provided between a gas supply unit and the work chamber, in order to secure the sterile environment in the work chamber. The air in the work chamber is discharged from a gas discharge unit through a particulate trap filter, which is provided between the work chamber and the gas discharge unit.

In addition, prior to the start of the subsequent work after a work is completed in the work chamber, the work chamber is sterilized by spraying therein, for example, hydrogen peroxide as a sterilizing substance from a sterilizing substance supply unit (see Japanese Patent Application Publication No. 2005-312799).

As a method for measuring the concentration of a sterilizing substance in an isolator, a system is known in which the concentration thereof in a sterilized chamber is measured in real time. This system is intended to check whether the transitional gas concentration satisfies the condition under which the sterilization is achieved (see Japanese Patent Application Publication No. 2008-68088). Another system is also known in which the temperature and humidity are measured in each of the gas flow upstream and the gas flow downstream of a hydrogen peroxide gas generator, the hydrogen peroxide gas being a sterilizing gas. This system is intended to determine the concentration of the hydrogen peroxide gas to be supplied into a sterilized chamber (see Japanese Patent Application Publication No. 2007-202628).

[Patent Document 1] Japanese Patent Application Publication No. 2006-68122
[Patent Document 2] Japanese Patent Application Publication No. 2005-218548
[Patent Document 3] Japanese Patent Application Publication No. 2005-312799
[Patent Document 4] Japanese Patent Application Publication No. 2008-68088
[Patent Document 5] Japanese Patent Application Publication No. 2007-202628

SUMMARY OF THE INVENTION

In the aforementioned circumstances, the present inventors have recognized the following challenges. In the structures described in the aforementioned Patent Documents 1 and 2, it is needed to start the generation of the hydrogen peroxide gas after the temperature of the heater, which is used for heating dried air or hydrogen peroxide solution itself, is heated to the desired temperature in order to stably generate hydrogen peroxide gas of a uniform concentration.

On the other hand, if heating of the heater is started during a leak test of an isolator, the pressure in the isolator varies due to the heat from the heater. Further, the pressure in the isolator varies due to the variation in the pressure in the space near the heater due to the heat from the heater. Therefore, a leak test with high reliability cannot be performed. Accordingly, it is needed to perform, at first, a leak test of an isolator, then to start the heating of a heater after the leak test is completed, and then to perform a sterilizing process by generating hydrogen peroxide gas after the heater has reached the desired temperature.

In an isolator, if a sterilizing process takes a long time, it also takes a long time before the isolator is in a state where the subsequent work can be started, thereby deteriorating the work efficiency. Accordingly, it is demanded that the time necessary for a sterilizing process be shortened in order to improve the work efficiency in an isolator. In the structures described in Patent Documents 1 and 2, the pre-heating of the heater is started after a leak test is completed, and hence there is room for shortening the time necessary for a sterilizing process.

In a conventional substitution step for hydrogen peroxide gas, the discharge amount of the gas is constant throughout the step without measuring the concentrations of the sterilizing substance during the discharge. Accordingly, the discharge amount is not controlled in accordance with the concentration of the sterilizing substance in the discharge air. Therefore, when performing discharge at a large discharge amount, a process for efficiently reducing the sterilizing substance is not performed in the first half of a substitution step by the equipment (a reduction process unit) for reducing the concentration of the sterilizing substance in the discharge air.

Accordingly, the non-reacted sterilizing substance is discharged into the air, thereby causing the problem that workers, etc., may be exposed to danger. On the other hand, when performing discharge at a small discharge amount, there occurs the problem that the discharge takes a too long time in the second half of the substitution step in which the concentration of the sterilizing substance in the isolator is decreased.

The present invention has been made based on such recognition by the present inventors, and a purpose of the invention is to provide a technique in which the time necessary for a sterilizing process in an isolator can be further shortened.

Another embodiment of the present invention has been made in view of these situations, and another purpose thereof is to provide a technique in which, when a sterilizing process is performed between the previous work and the subsequent work in an isolator, the isolator is set to the state in an earlier time where the subsequent work can be started, and a technique in which discharge amount of a sterilizing substance into the air can be reduced.

An embodiment of the present invention is an isolator. The isolator comprises: a work chamber for performing a work in which a biomaterial is handled; a sterilizing substance supply unit that is provided in a state independent from a gas flow channel including the work chamber in terms of heat and pressure, and that has a heater for heating a sterilizing substance to be vaporized, and that is configured to supply the vaporized sterilizing substance into the gas flow channel; a gas flow channel pressure adjustment unit configured to increase or decrease the pressure in the gas flow channel; a gas flow channel pressure detector configured to detect the pressure inside the gas flow channel; and a controller configured to control execution of a gas flow channel leak test for checking a gas leak in the gas flow channel based on a detection result by the gas flow channel pressure detector after making the gas flow channel pressure adjustment unit increase or decrease the pressure in the gas flow channel, and configured to control supply of the sterilizing substance by the sterilizing substance supply unit, in which the controller performs heating of a heater, which accompanies the supply of the sterilizing substance, in parallel with the gas flow channel leak test.

According to this embodiment, the time necessary for a sterilizing process in an isolator can be further shortened.

In the aforementioned embodiment, the isolator may comprise: a supply unit pressure adjustment unit configured to increase or decrease the pressure in the sterilizing substance supply unit; and a supply unit pressure detector configured to detect the pressure in the sterilizing substance supply unit, in which the controller makes the supply unit pressure adjustment unit increase or decrease the pressure in the sterilizing substance supply unit when the heater is at normal temperature, and in which the controller controls execution of a supply unit leak test for checking a gas leak in the sterilizing substance supply unit based on a detection result by the supply unit pressure detector.

Another embodiment of the present invention is also an isolator. The isolator comprises: a work chamber for performing a work in which a biomaterial is handled; a gas supply unit configured to supply a gas into the work chamber; a gas discharge unit configured to discharge the gas from the work chamber; a connection channel that has a particulate trap filter and connects the gas supply unit with the work chamber; a sterilizing substance supply unit configured to supply a sterilizing substance into the work chamber; a discharge means configured to control the discharge amount of the gas that is discharged from the gas discharge unit; a reduction process unit configured to reduce the concentration of the sterilizing substance that is contained in the gas discharged from the gas discharge unit; and a controller configured to start discharge by using the discharge means after sterilizing the inside of the work chamber by supplying the sterilizing substance into the work chamber to maintain the concentration of the sterilizing substance in the work chamber, and configured to make the discharge amount at the end of the discharge larger than that occurring when the concentration of the sterilizing substance reaches the maximum.

According to this embodiment, when performing a sterilizing process between the previous work and the subsequent work in an isolator, the isolator can be set to the state in an earlier time where the subsequent work can be started by an efficient substitution step. Further, when the sterilizing substance in the discharge gas reaches a predetermined concentration, the discharge amount is suppressed, and hence it can be suppressed to the minimum that the sterilizing substance, which has not been treated by the sterilizing substance reduction process unit, may be discharged into the air. As a result, the safety of a worker can be improved.

In the aforementioned another embodiment, the isolator may further comprise a concentration measurement unit that is provided in the gas discharge unit and configured to measure the concentration of the sterilizing substance remaining in the gas that is discharged from the gas discharge unit, in which the controller gradually increases the discharge amount before the concentration, which has been measured by the concentration measurement unit, reaches a predetermined determination concentration such that the discharge amount is maintained within a predetermined range after the concentration has reached the determination concentration, and the controller further gradually increases the discharge amount on condition that a reduction rate of the concentration, which has been measured by the concentration measurement unit, exceeds a predetermined threshold value.

Further, in the aforementioned another embodiment, the isolator may further comprise a concentration measurement unit that is provided in the gas discharge unit and configured to measure the concentration of the sterilizing substance remaining in the gas that is discharged from the gas discharge unit, in which the controller controls the discharge amount by feedback using the concentration, which has been measured by the concentration measurement unit, so that the discharge amount is gradually increased before the concentration reaches a predetermined determination concentration and that the concentration of the sterilizing substance in the discharge gas is within a predetermined range after the concentration has reached the determination concentration, and the controller fixes the discharge amount on condition that the discharge amount has reached a predetermined discharge amount.

Also, in the aforementioned another embodiment, when the concentration measurement unit is provided on the gas flow downstream side of the reduction process unit, the isolator may further comprise another concentration measurement unit, which is provided on the gas flow upstream side thereof, in which the controller measures, by using the another measurement unit, the concentration of the sterilizing substance in the discharge gas before being subjected to the reduction process on condition that the concentration of the sterilizing substance in the discharge gas after being subjected to the reduction process has reached the detection limit of the concentration measurement unit, the concentration being measured by the concentration measurement unit, and wherein the controller ends the discharge by the gas discharge unit on condition that the concentration of the sterilizing substance, which has been measured by the another concentration measurement unit, has reached the detection limit of the another concentration measurement unit.

In the aforementioned another embodiment, the isolator may comprise a measurement unit configured to measure the time elapsed since the discharge of the gas in the work chamber is started until the concentration of the sterilizing substance reaches the detection limit of the concentration measurement unit, in which the controller communicates that the capability of the reduction process unit is decreased when the measured time exceeds a predetermined threshold value.

In the aforementioned another embodiment, the sterilizing substance may be hydrogen peroxide.

Appropriate combinations of the aforementioned each component can be encompassed by the scope of the present invention seeking the protection of the patent by the present patent application.

EFFECT OF THE INVENTION

According to the present invention, the time necessary for a sterilizing process in an isolator can be further shortened.

Also, according to the another embodiment of the present invention, discharge of a sterilizing substance into the air can be reduced as well as the time necessary for a sterilizing process being shortened.

BRIEF DESCRIPTION OF THE DRAWINGS

Embodiments will now be described, byway of example only, with reference to the accompanying drawings which are meant to be exemplary, not limiting, and wherein like elements are numbered alike in several Figures, in which.

Figure 1:
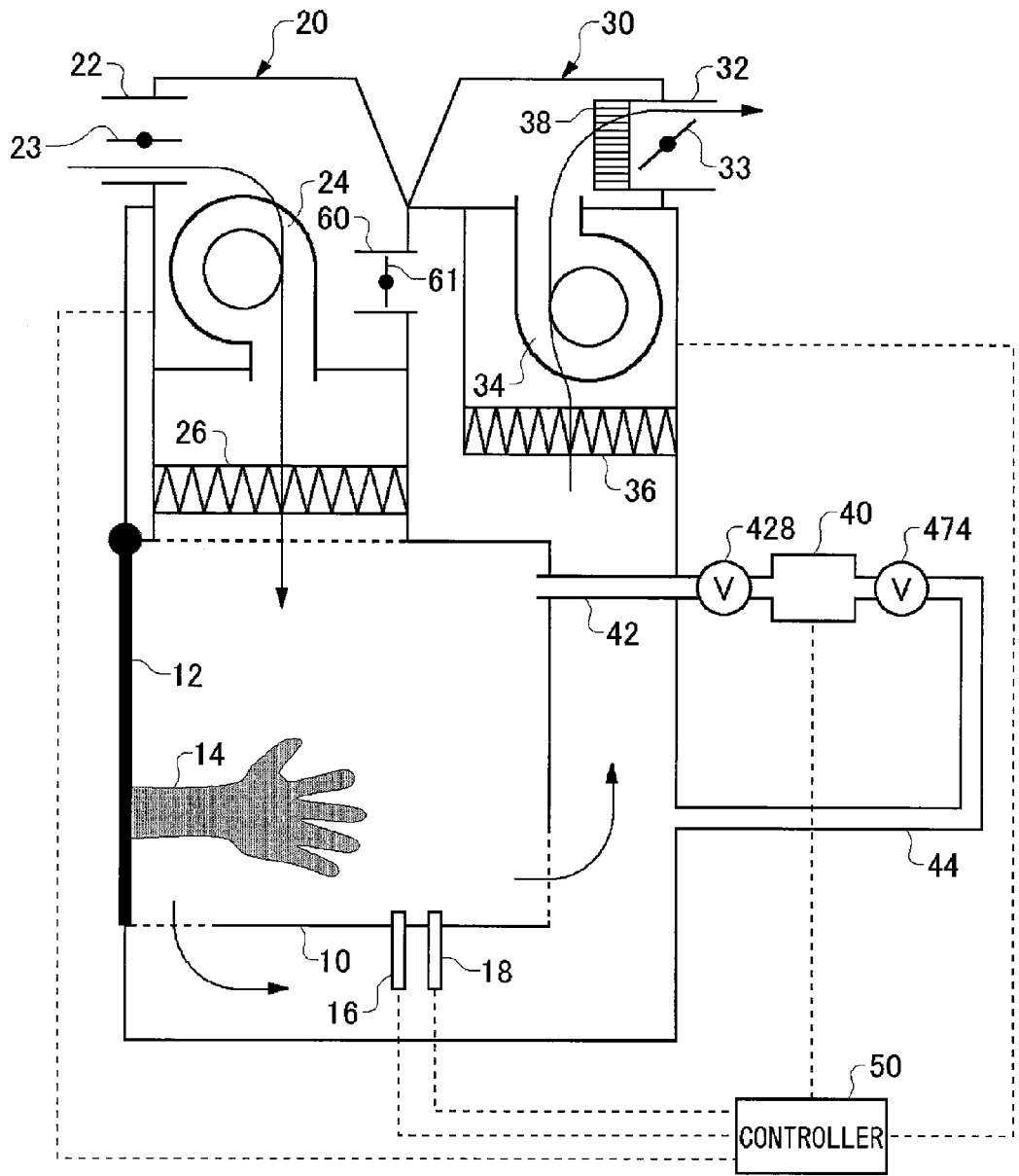
FIG. 1 is a schematic view illustrating the structure of an isolator according to Embodiment 1.

REFERENCE NUMERALS 10, 1010 WORK CHAMBER
16 WORK CHAMBER THERMOMETER
18 WORK CHAMBER BAROMETER
20, 1040 GAS SUPPLY UNIT
22, 1042 INTAKE VENT
23 INTAKE VALVE
24 INTAKE FAN
26 PARTICULATE TRAP FILTER
30, 1050 GAS DISCHARGE UNIT
32, 1058 DISCHARGE VENT
33 DISCHARGE VALVE
34 DISCHARGE FAN
36 PARTICULATE TRAP FILTER
38 STERILIZING SUBSTANCE REMOVAL FILTER
40, 1030 STERILIZING SUBSTANCE SUPPLY UNIT
42, 1033, 1035 STERILIZING SUBSTANCE SUPPLY PIPE
44 STERILIZING SUBSTANCE CIRCULATION CHANNEL
50, 1090 CONTROLLER
60 CIRCULATION VENT
61 CIRCULATION CHANNEL VALVE
100, 1100, 1300 ISOLATOR
402 STERILIZING GAS GENERATOR
410 ATOMIZING UNIT
413 ULTRASONIC TRANSDUCER
414 CUP
419 SUPPLY UNIT BAROMETER
420 VAPORIZATION UNIT
421 HEATING PIPE
422 HEATER
423 FLOW CHANNEL FORMATION BOARD
424 PIPE
425 THERMOMETER
427, 475 HEAT-INSULATING CONNECTION PORTION
428, 474 VALVE
460 HYDROGEN PEROXIDE SOLUTION CARTRIDGE
462 PIPE
464, 1034 PUMP
470 AIR SUPPLY FAN
1012 FRONT DOOR
1014 WORK GLOVE
1016 GAS SUPPLY VENT
1018 GAS DISCHARGE VENT
1020, 1022 HEPA FILTER
1032 STERILIZING SUBSTANCE SUPPLY TANK
1036 STERILIZING SUBSTANCE SENDING UNIT
1044, 1052 THREE-WAY VALVE
1046 FAN
1054 STERILIZING SUBSTANCE REDUCTION PROCESS UNIT
1056, 1060 CONCENTRATION MEASUREMENT UNIT
1070, 1072, 1074, 1076, 1078, 1080, 1082 CHANNEL
1092 MEASUREMENT UNIT
1094 RECORDING UNIT
1202 CONTROL SUBSTRATE
1203 HYDROGEN PEROXIDE GAS (MIST)
1204 HYDROGEN PEROXIDE SOLUTION TANK
1206 WATER SEAL CAP

DETAILED DESCRIPTION OF THE INVENTION

Hereinafter, the present invention will be described with reference to the drawings based on the preferred embodiments of the invention. The same or like components, members, or processes illustrated in each drawing are denoted by like reference numerals, and the duplicative descriptions will be appropriately omitted. The embodiments are not intended to limit the invention but to serve as particular examples thereof, and all features or combinations thereof described there are not always essential to the present invention.

Embodiment 1

FIG. 1 is a schematic view illustrating the structure of an isolator 100 according to Embodiment 1.

As illustrated in FIG. 1, the isolator 100 according to Embodiment 1 comprises a work chamber 10, a gas supply unit 20, a gas discharge unit 30, a sterilizing substance supply unit 40, and a controller 50.

The work chamber 10 is a space for performing a work in which a biomaterial is handled, such as cell extraction and cell culture. A front door 12 is provided in the work chamber 10 in an openable and closable manner, and work gloves 14 for performing a work within the work chamber 10 are provided at certain positions of the front door 12. A worker can perform, through the work gloves 14, a work within the work chamber 10 after inserting his/her hands from not-illustrated openings that are provided on the front door 12. Herein, the biomaterial means a material that includes a living organism itself including cells, a substance of which a living organism is composed, or a substance that is produced by a living organism. In addition, a work chamber thermometer 16 for detecting the temperature inside the work chamber 10, and a work chamber barometer 18, as a gas flow channel pressure detector for detecting the pressure inside the gas flow channel including the work chamber 10, are provided in the work chamber 10.

The gas supply unit 20 comprises an intake vent 22 and an intake fan 24, such as a Sirocco fan, and takes in the gas outside the isolator 100 from the intake vent 22 by the intake fan 24 to supply the gas into the isolator 100. A particulate trap filter 26, such as HEPA (High Efficiency Particulate Air) filter, is provided in the connection portion in the gas supply unit 20, the connection portion being connected with the work chamber 10. An intake valve 23 is provided in the intake vent 22 in an openable and closable manner, thereby intake of the outside air from the intake vent 22 being controlled by opening and closing of the intake valve 23. In addition, a circulation vent 60 is provided in the gas supply unit 20, and a circulation channel valve 61 is provided in the circulation vent 60 in an openable and closable manner.

The gas discharge unit 30 comprises a discharge vent 32 and a discharge fan 34, such as a Sirocco fan, and discharges, from the discharge vent 32, the gas within the work chamber 10 to the outside of the isolator 100. A particulate trap filter 36, such as HEPA filter, is provided on the gas flow upstream side of the discharge fan 34 in the gas discharge unit 30. A discharge valve 33 is provided in the discharge vent 32, thereby discharge of the gas from the discharge vent 32 being controlled by opening and closing of the discharge valve 33. In addition, a sterilizing substance removal filter 38, which includes activated carbon and platinum catalyst, etc., is provided on the gas flow upstream side of the discharge valve 33 in the discharge vent 32. In the isolator 100 according to the present embodiment, a gas flow channel pressure adjustment unit, which is used for increasing or decreasing the pressure in the gas flow channel including the work chamber 10, is structured with the intake fan 24 and the discharge fan 34. Herein, the gas flow channel including the work chamber 10 means the area from the intake vent 22 to the discharge vent 32, which include, for example, the gas supply unit 20 and the gas discharge unit 30.

The sterilizing substance supply unit 40 is used for supplying a vaporized sterilizing substance into the inside of the gas flow channel including the work chamber 10. One end of the sterilizing substance supply unit 40 is connected with the work chamber 10 through a sterilizing substance supply pipe 42 and the other end thereof is connected, through a sterilizing substance circulation channel 44, with the gas flow channel between the work chamber 10 and the gas discharge unit 30. A valve 428 is provided in the sterilizing substance supply pipe 42, and a valve 474 is provided in the sterilizing substance circulation channel 44. In the isolator 100, the inside of the gas flow channel including the work chamber 10 can be under a sterile environment by supplying a sterilizing substance from the sterilizing substance supply unit 40. Herein, the sterile environment means an environment as close to the dust-free, sterile environment as possible in order to prevent contamination of a substance other than the substances that are necessary for the work performed in the work chamber.

Figure 2:
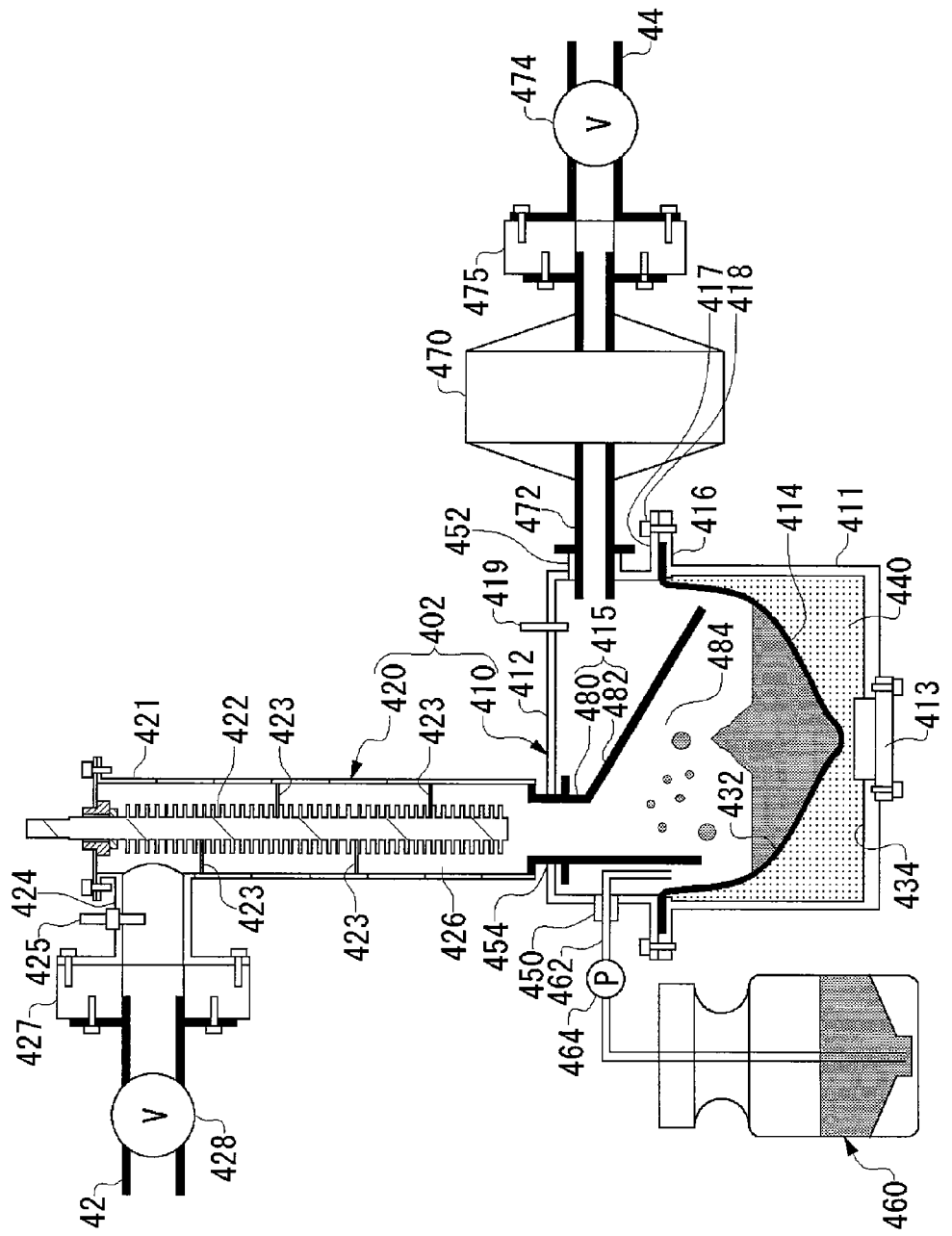
FIG. 2 is a schematic view illustrating the structure of a sterilizing substance supply unit.

In the present embodiment, the sterilizing substance is hydrogen peroxide and the sterilizing substance supply unit 40 has, for example, the structure that is illustrated in FIG. 2. FIG. 2 is a schematic view illustrating the structure of the sterilizing substance supply unit 40.

As illustrated in FIG. 2, the sterilizing substance supply unit 40 has a sterilizing gas generator 402 that is composed of an atomizing unit 410 and a vaporization unit 420, a hydrogen peroxide solution cartridge 460 that stores a hydrogen peroxide solution, and an air supply fan 470 that serves as a supply unit pressure adjustment unit.

The atomizing unit 410 has a housing member 411, a cover member 412, an ultrasonic transducer 413, a cup 414, and a funnel member 415.

The ultrasonic transducer 413 is provided on the bottom surface of the housing member 411. The ultrasonic transducer 413 is a device that transforms electric energy into machinery vibrations of an ultrasonic range. A supply unit barometer 419 is provided on the upper surface of the cover member 412 as a supply unit pressure detector that detects the pressure inside the sterilizing substance supply unit 40.

A flange 416 is formed on the upper outer circumference of the housing member 411. In addition, a flange 417 is formed, corresponding to the flange 416, on the lower outer circumference of the cover member 412. The gap between the flanges 416 and 417 is sealed by fastening the flanges 416 and 417 with fastening members 418, such as screws, so that a space is formed inside the housing member 411 and the cover member 412.

The internal space of the housing member 411 and the cover member 412 is partitioned into an upper space 432 and a lower space 434 by the cup 414. Specifically, the periphery of the cup 414 is inserted between the flanges 416 and 417 so as to be fixed by fastening the flanges 416 and 417 with the fastening members 418.

Ultrasonic wave propagation liquid 440, which propagates machinery vibrations of an ultrasonic range generated by the ultrasonic transducer 413, is filled in the lower space 434. As the ultrasonic wave propagation liquid 440, liquid with a low viscosity, such as water, is preferred. On the other hand, a funnel member 415, which is formed of a pipe 480 and a funnel-shaped portion 482, is provided in the upper space 432. The funnel member 415 will be described later.

Openings 450 and 452 are provided on the side surface of the cover member 412. In addition, an opening 454 is provided on the upper surface of the cover member 412. A pipe 462, which is used for supplying, into the space 432, the hydrogen peroxide solution that is stored in the hydrogen peroxide solution cartridge 460, is inserted into the opening 450. A pump 464, which is used for pumping the hydrogen peroxide solution that is stored in the hydrogen peroxide solution cartridge 460, is provided in the middle of the pipe 462. As the pump 464, a pump, such as a Peristalic pump, is preferred, by which the channel inside the pipe 462 is shielded in an airtight manner such that the inside of the sterilizing substance supply unit can be maintained in an airtight manner during a leak test of the supply unit, which will be described later. When the pump 464 has a structure in which the channel inside the pipe 462 is not shielded in an airtight manner, the channel thereof may be shielded in an airtight manner by, for example, providing a shield means, such as a valve, at a position of the pipe 462 between the pump 464 and the hydrogen peroxide solution cartridge 460.

In addition, a pipe 472 for sending, into the space 432, the air sent from an air supply fan 470, such as an axial fan, which is provided in the middle of the pipe 472, is connected with the opening 452. The other end of the pipe 472, opposite to the opening 452, is connected with the sterilizing substance circulation channel 44 through a heat-insulating connection portion 475, which is made from a heat-insulating resin, etc. A valve 474 is provided in the end area on the heat-insulating connection portion 475 side of the sterilizing substance circulation channel 44. Accordingly, the sterilizing substance circulation channel 44 side of the sterilizing substance supply unit 40 is provided, by the heat-insulating connection portion 475 and the valve 474, in a state independent from the gas flow channel including the work chamber 10 in terms of heat and pressure. The air supply fan 470 also serves as a supply unit pressure adjustment unit that increases the pressure in the sterilizing substance supply unit 40 by sending air into the space 432 with positive rotation and that decreases the pressure therein by sucking in the air from the space 432 with negative rotation. The air supply fan 470 is used for supplying the sterilizing substance into the work chamber 10.

The pipe 480 of the funnel member 415 is inserted into the opening 454 and the funnel member 415 is fixed such that an opening 484 of the funnel-shaped portion 482 is directed downwards. The other end of the pipe 480 is fixed to the vaporization unit 420. The opening 452 is provided at a position higher than that of the opening 484 of the funnel-shaped portion 482. Thereby, it is designed that the air sent from the opening 452 flows downwards along the outside of the funnel-shaped portion 482 without directly blowing into the opening 484, and after turning back at the lower position of the funnel-shaped portion 482, the air flows upwards along the inside of the funnel-shaped portion 482.

In the atomizing unit 410 structured as stated above, the hydrogen peroxide solution, which has been supplied into the cup 414, is atomized by the machinery vibrations of an ultrasonic range, and the atomized hydrogen peroxide is sent, by the air sent from the air supply fan 470, into the vaporization unit 420 through the opening 484 of the funnel-shaped portion 482 and the pipe 480. Because the funnel member 415 is provided in the connection portion between the space 432 and the vaporization unit 420 and the opening 484 is funnel-shaped, the atomized hydrogen peroxide is efficiently trapped to be sent into the vaporization unit 420. In this case, the hydrogen peroxide with a relatively large particle shape, which is adhering to the inside of the funnel-shaped portion 482 without being atomized, falls on the cup 414 due to gravity to be atomized again.

The vaporization unit 420 has a heating pipe 421, a heater 422, a flow channel formation board 423, a pipe 424, and a thermometer 425.

The heating pipe 421 is connected with the pipe 480 such that the axial direction thereof is directed vertically. A flow channel 426 is formed inside the heating pipe 421, through which the hydrogen peroxide and the air, which have been sent from the pipe 480, flow from downward to upward. The flow channel formation boards 423, which protrude from the inside of the heating pipe 421 in the direction perpendicular to the axis of the heating pipe 421, are alternately provided inside the heating pipe 421. Thereby, the flow channel 426, which is provided inside the heating pipe 421, meanders and becomes long. As a result, the hydrogen peroxide remains in the flow channel 426 for a longer time, thereby ensuring that the hydrogen peroxide is gasified within the flow channel 426.

In the present embodiment, the heating pipe 421 is provided immediately above the space 432. Accordingly, when the hydrogen peroxide is liquefied within the heating pipe 421 without being gasified, the liquefied hydrogen peroxide falls into the space 432 due to gravity. The hydrogen peroxide, which has returned into the space 432, is again atomized by the machinery vibrations of a ultrasonic range to be sent into the heating pipe 421. Thereby, the hydrogen peroxide within the cup 414 can be surely gasified without waste by returning, with a simplified structure, the hydrogen peroxide that has been liquefied within the heating pipe 421 so as to be atomized again.

The heater 422 for heating the atomized hydrogen peroxide to be vaporized is provided at the center portion of the heating pipe 421 and along the axis of the heating pipe 421. The heater 422 can be heated, for example, up to 150° C. that is appropriate for the vaporization of the hydrogen peroxide, and the temperature thereof is adjusted with on/off control by the controller 50. It is desirable that a plurality of fins are provided in the heater 422. Thereby, the contact area between the heater 422 and the hydrogen peroxide, flowing through the flow channel 426, can be increased such that the gasification of the hydrogen peroxide is promoted.

One end of the pipe 424 is connected with the upper side surface of the heating pipe 421. A thermometer 425 for measuring the internal temperature of the pipe 424 is provided in the pipe 424. The other end of the pipe 424 is connected with the sterilizing substance supply pipe 42 through a heat-insulating connection portion 427, which is made from a heat-insulating resin, etc. A valve 428 is provided in the end area on the heat-insulating connection portion 427 side of the sterilizing substance supply pipe 42. Accordingly, the sterilizing substance supply pipe 42 side of the sterilizing substance supply unit 40 is provided, by the heat-insulating connection portion 427 and the valve 428, in a state independent from the flow channel including the work chamber 10 in terms of heat and pressure.

In the sterilizing substance supply unit 40 structured as stated above, the operations for supplying a sterilizing gas will be described.

The heater 422 is at first switched on such that heating of the heater 422 is started and the pump 464 is driven such that the hydrogen peroxide stored in the hydrogen peroxide solution cartridge 460 is pumped up, thereby sending the hydrogen peroxide toward the space 432.

The internal temperature of the pipe 424 starts to rise from normal temperature by switching on the heater 422. Further, when the hydrogen peroxide solution reaches the space 432 through the pipe 462, the hydrogen peroxide solution starts to accumulate on the bottom of the cup 414, and the amount of the sterilizing substance solution within the cup 414 starts to rise.

When the thermometer 425 for measuring the internal temperature within the pipe 424 reaches the temperature at which the hydrogen peroxide gas is not recondensed, for example 90° C., the ultrasonic transducer 413 is driven such that machinery vibrations of an ultrasonic range are propagated into the space 432 through the ultrasonic wave propagation liquid 440. In addition, air blasting is started by the air supply fan 470 such that the air within the gas flow channel is sent into the space 432 through the sterilizing substance circulation channel 44. Thereby, the hydrogen peroxide is atomized in the space 432, and the atomized hydrogen peroxide is supplied into the heating pipe 421 by the air blast from the air supply fan 470. The atomized hydrogen peroxide, which has been supplied into the heating pipe 421, is gasified by heating with the heater 422. The gasified hydrogen peroxide is supplied into the sterilizing substance supply pipe 42 through the pipe 424.

It is desirable that the flow amount of the hydrogen peroxide solution, which is to be sent toward the space 432 by the pump 464, is controlled such that the amount of the hydrogen peroxide solution in the cup 414 is appropriate for being atomized by the machinery vibrations of a ultrasonic range. Thereby, the hydrogen peroxide solution in the cup 414 can be efficiently atomized.

When the hydrogen peroxide solution does not remain in the hydrogen peroxide solution cartridge 460 by being gradually consumed, the supply of the hydrogen peroxide solution into the space 432 is stopped. After the supply of the hydrogen peroxide solution into the upper space 432 is stopped, the amount of the hydrogen peroxide solution in the cup 414 is gradually decreased, and finally the residue of the hydrogen peroxide solution in the cup 414 becomes zero.

When the residue of the hydrogen peroxide solution in the cup 414 becomes zero, the amount of the atomized hydrogen peroxide, which is to be sent from the atomizing unit 410 to the vaporization unit 420, is gradually decreased, and hence the heat amount, which is consumed by the vaporization of the hydrogen peroxide, is gradually decreased. Thereby, the internal temperature within the pipe 424 further rises from the vaporization temperature of the hydrogen peroxide.

When the internal temperature within the pipe 424, which has been measured by the thermometer 425, has reached a predetermined determination temperature, the heater 422 is switched off such that the heating of the heater 422 is stopped. The determination temperature means the internal temperature within the pipe 424 at which only the air starts moving through the heating pipe 421 after the gasification of the hydrogen peroxide within the heating pipe 421 has been completed. That is, the fact that the internal temperature within the pipe 424 reaches a predetermined determination temperature means that the residue of the hydrogen peroxide solution in the cup 414 becomes zero and the hydrogen peroxide solution to be gasified no longer remains in the sterilizing substance supply unit 40. After the heater 422 is turned off, the internal temperature within the pipe 424 gradually falls and then returns to normal temperature.

The structure of the sterilizing substance supply unit 40 shall not be limited to the aforementioned one, but may be one in which hydrogen peroxide gas is generated by, for example, supplying the hydrogen peroxide solution into a heated container to be vaporized. In addition, a sterilizing substance shall not be limited to hydrogen peroxide, but may be a substance containing, for example, an active oxygen species, such as ozone.

The controller 50 controls: opening/closing of the intake valve 23, the discharge valve 33, and the circulation channel valve 61; on/off of the intake fan 24 and the discharge fan 34; drive of the pump 464 in the sterilizing substance supply unit 40; opening/closing of the valves 428 and 474; and on/off of the heater 422, the air supply fan 470, and the ultrasonic transducer 413.

Figure 3:
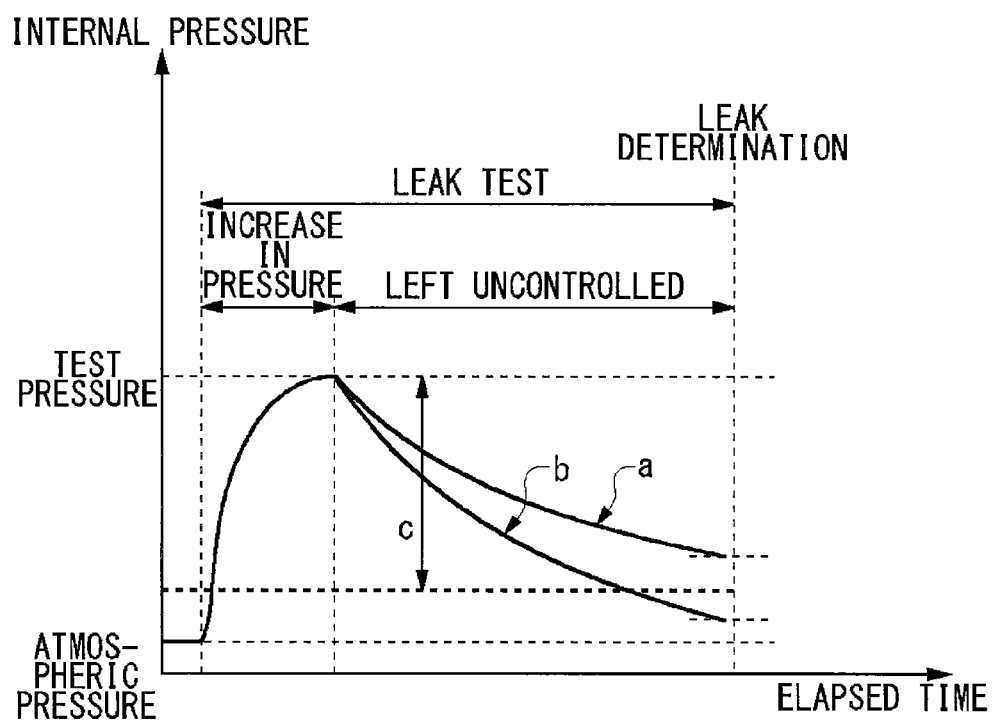
FIG. 3 is a graph for explaining a leak test of the isolator.
Figure 4:
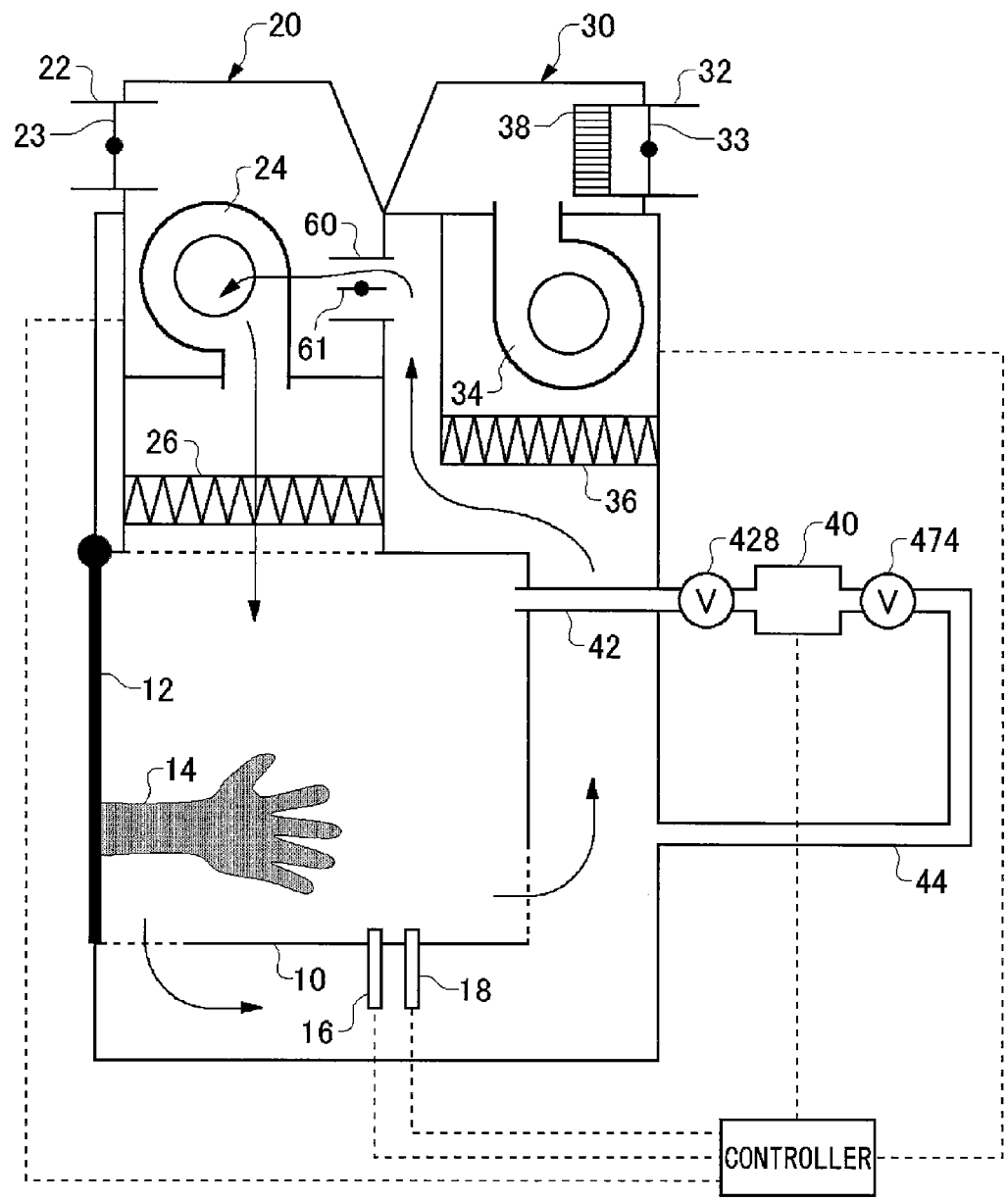
FIG. 4 is a view illustrating the state of the isolator when a sterilizing substance is supplied.

Subsequently, the sterilizing process in the isolator 100, which is structured as stated above, will be described. FIG. 3 is a graph for explaining a leak test of the isolator 100. FIG. 4 is a view illustrating the state of the isolator 100 when a sterilizing substance is supplied.

In the state where a work is being performed in the work chamber 10, the controller 50 controls the intake valve 23 and the discharge valve 33 so as to be in open states, and controls the circulation channel valve 61 so as to be in a closed state, as illustrated in FIG. 1. Further, the controller 50 makes the intake fan 24 and the discharge fan 34 drive. Thereby, as illustrated by the arrows in FIG. 1, a gas flow channel is formed in the isolator 100 in which the open air is supplied into the work chamber 10 from the intake vent 22 and the gas in the work chamber 10 is discharged outside the isolator 100 from the discharge vent 32.

In the isolator 100, before the start of the first work, after the end of a work (previous work) within the work chamber 10, and before the start of the subsequent work, a sterilizing process for sterilizing the inside of the gas flow channels including the work chamber 10 is performed. The sterilizing process in the isolator 100 includes a pretreatment step, a sterilizing step, and a removal step.

In the pretreatment step, a gas flow channel leak test is performed under the control of the controller 50, in which a gas leak in the gas flow channel including the work chamber 10, which is to be filled with hydrogen peroxide gas, is checked. Hereinafter, the gas flow channel leak test will be described with reference to FIG. 3.

In the gas flow channel leak test, the intake fan 24 is turned on in the state where the intake valve 23 is in an open state and the discharge valve 33 is in a closed state, thereby the open air being taken into the inside of the gas flow channel in the isolator 100. At the time, the valves 428 and 474 are set to closed states. Thereby, the pressure within the gas flow channel is increased. The pressure in the gas flow channel is almost the same as that in the work chamber 10, which can be detected by the work chamber barometer 18. The controller 50 detects, from a detection result by the work chamber barometer 18, that the pressure in the gas flow channel has reached the test pressure, which is necessary for the leak test. When the pressure in the gas flow channel reaches the test pressure, the controller 50 closes the intake valve 23 and turns off the intake fan 24. Alternatively, it may be designed that the gas flow channel has a negative pressure by driving the discharge fan 34 in the state where the intake valve 23 is in a closed state and the discharge valve 33 is in an open state.

Subsequently, the state of the isolator 100 is maintained as it is for a certain period, for example, 10 minutes. After the certain period has passed, the controller 50 determines whether a leak occurs based on a detection result by the work chamber barometer 18. When the pressure in the gas flow channel after the certain period exceeds the acceptable pressure decrease c (curve a), the controller 50 continues the sterilizing process. On the other hand, when the pressure in the gas flow channel after the certain period is below the acceptable pressure decrease c (curve b), the controller 50 discontinues the sterilizing process and communicates the discontinuation of the sterilizing process to a worker by presenting that a gas leak has occurred with a non-illustrated information unit. With the aforementioned procedures, the gas flow channel leak test is completed.

Also, in the pretreatment step, the heater 422 is switched on such that heating of the heater 422 is started. In a conventional isolator, an accurate gas flow channel leak test cannot be performed because: when heating of the heater 422 is started during the gas flow channel leak test, the pressure in the gas flow channel varies due to the heat from the heater 422; and the pressure in the gas flow channel further varies due to the variation in the pressure within the sterilizing substance supply unit 40 due to the heat from the heater 422. Accordingly, it is needed to start heating of the heater 422 after the gas flow channel leak test is completed. On the other hand, in the isolator 100 according to the present embodiment, the gas flow channel and the sterilizing substance supply unit 40, including the heater 422, are connected, through the heat-insulating connection portions 427 and 475 and the valves 428 and 474, in a state independent from each other in terms of heat and pressure. Therefore, heating of the heater 422 can be started during the gas flow channel leak test.

As illustrated in FIG. 4, when the temperature of the heater 422 has reached a predetermined temperature, the intake valve 23 and the discharge valve 33 are set to closed states, the circulation channel valve 61 is set to an open state, and the intake fan 24 is turned on. And also, the valves 428 and 474 are set to open states such that generation of the hydrogen peroxide gas is started. The generated hydrogen peroxide gas is supplied into the work chamber 10 through the sterilizing substance supply pipe 42 and circulates within the gas flow channel as illustrated by the arrows in FIG. 4. Herein, the predetermined temperature means the internal temperature within the pipe 424 at which the hydrogen peroxide gas is not recondensed.

When the hydrogen peroxide gas is supplied into the gas flow channel and the concentration of the hydrogen peroxide gas within the gas flow channel, including the work chamber 10, is greater than or equal to the concentration that is necessary for the sterilizing process, the sterilizing step is started. As illustrated in FIG. 4, in the sterilizing step, the hydrogen peroxide gas, which has been sent from the sterilizing substance supply unit 40, circulates along the route of the work chamber 10, the circulation vent 60, the discharge fan 34, and the work chamber 10 such that these areas are sterilized, in the state where the intake valve 23 and the discharge valve 33 are set to closed states and the circulation channel valve 61 is set to an open state. The sterilizing process enters the removal step after the sterilizing step is completed.

In the removal step, the supply of the hydrogen peroxide gas from the sterilizing substance supply unit 40 is stopped, and the intake valve 23 and the discharge valve 33 are set to open states, the circulation channel valve 61 is set to a closed state, and the intake fan 24 and the discharge fan 34 are turned on. Thereby, air outside the isolator 100 is taken in from the intake vent 22 to be supplied into the gas flow channel. And also, the hydrogen peroxide gas within the gas flow channel is sent into the gas discharge unit 30 to be removed by being adsorbed with the sterilizing substance removal filter 38 or by being degraded.

When air is substituted for the gas in the gas flow channel and the concentration of the hydrogen peroxide gas in the gas flow channel becomes smaller than or equal to a predetermined concentration in the removal step, the work chamber is in the state of being able to be used and the sterilizing process is completed. Herein, the concentration of the hydrogen peroxide gas at which the work chamber 10 is in the state of being able to be used means the concentration at which the biomaterial, which is used in a work, is not affected to the extent that cannot be neglected for the work. The concentration is, for example, smaller than or equal to 1 ppm (TWA: Time Weighted Average) that is specified by ACGIH (American Conference of Government Industrial Hygienists).

Herein, a collective leak test can be performed by executing the same steps as in the aforementioned gas flow channel leak test with the valves 428 and 474 being set to open states, in which a gas leak in the total space of the gas flow channel and the sterilizing substance supply unit 40 can be checked. Alternatively, the collective leak test may be performed by executing the same steps as in a supply unit leak test, which will be described later, with the valves 428 and 474 being set to open states.

Subsequently, the supply unit leak test will be described. In the isolator 100 according to the present embodiment, a supply unit leak test is performed in addition to the gas flow channel leak test and the collective leak test, in which a gas leak in the sterilizing substance supply unit 40 is checked independently from the gas leak in the gas flow channel. In the isolator 100 according to the embodiment, the sterilizing substance supply unit 40 is provided with the air supply fan 470 and the supply unit barometer 419, and the gas flow channel, including the work chamber 10, and the sterilizing substance supply unit 40 are, by the valves 428 and 474, independent from each other in terms of pressure. Therefore, the supply unit leak test can be performed independently from the gas flow channel leak test.

In the supply unit leak test, the valve 428 is set to a closed state, the valve 474 is set to an open state, and the air supply fan 470 is turned on, so that air is taken into the sterilizing substance supply unit 40. The air tightness of the pipe 462 is maintained by the pump 464 or the aforementioned shield means. Thereby, the pressure in the sterilizing substance supply unit 40 is increased. The pressure in the sterilizing substance supply unit 40 is detected by the supply unit barometer 419. The controller 50 detects, from a detection result by the supply unit barometer 419, that the pressure in the sterilizing substance supply unit 40 has reached the test pressure, which is necessary for the leak test. When the pressure in the sterilizing substance supply unit 40 has reached the test pressure, the controller 50 closes the valve 474 and turns off the air supply fan 470. Alternatively, it may be designed that the sterilizing substance supply unit 40 has a negative pressure by driving the air supply fan 470 in the state where the valves 428 and 474 are set to open states.

Subsequently, the state of the sterilizing substance supply unit 40 is maintained as it is for a certain period, for example, 10 minutes. After the certain period has passed, the controller 50 determines, in the same way as in the gas flow channel leak test, whether a leak occurs based on a detection result by the supply unit barometer 419. When the pressure in the sterilizing substance supply unit 40 after the certain period exceeds the acceptable pressure decrease, the controller 50 continues the process to be subsequently performed. In contrast, when the pressure is below the acceptable pressure decrease, the controller 50 communicates to a worker.

Figure 5:
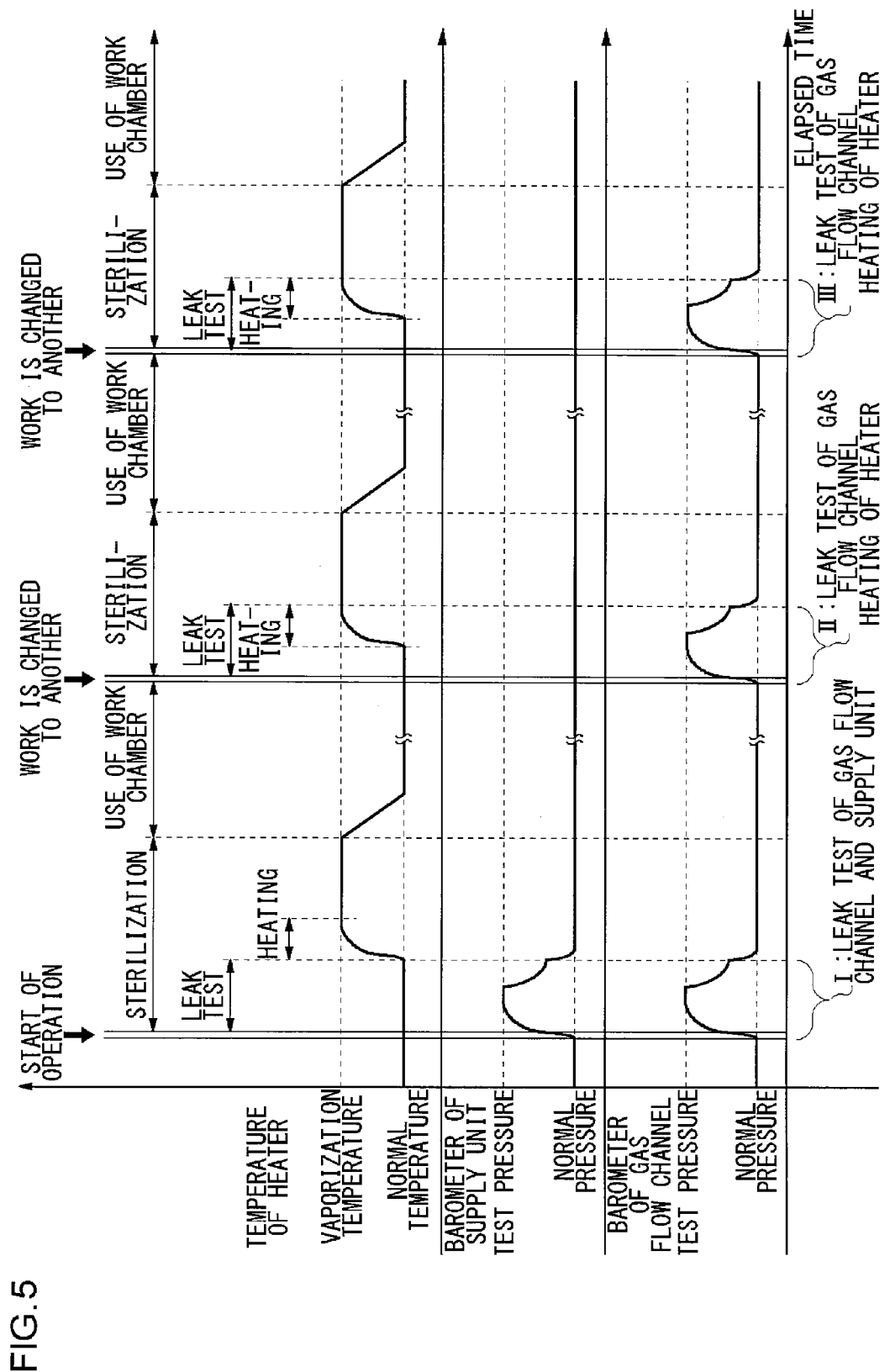
FIG. 5 is a graph explaining check timing of a gas leak in the sterilizing substance supply unit.

A gas leak in the sterilizing substance supply unit 40 is checked by the collective leak test or the supply unit leak test, for example, at the following timing. FIG. 5 is a graph explaining the check timing of a gas leak in the sterilizing substance supply unit 40.

Because the gas flow channel including the work chamber 10 has a portion, the sealing of which is secured by a manual operation, such as the front door 12, it is desirable that a gas flow channel leak test is performed at every sterilizing process. On the other hand, the gas leak in the sterilizing substance supply unit 40, which does not satisfy the standard of the supply unit leak test, may occur only due to the aging degradation of the non-illustrated packing, which are provided, for example, in the openings 450, 452, and 454, etc. Therefore, the safety of the isolator 100 can be secured even when the gas leak check of the sterilizing substance supply unit 40 is not performed so often as the gas flow channel leak test.

Accordingly, in the isolator 100 according to the present embodiment, it is designed that the gas leak check of the sterilizing substance supply unit 40 is periodically performed while the heater 422 is being at normal temperature, as illustrated in FIG. 5. That is, it is designed that, of the works in a day, the collective leak test is performed before the first work is started (during the timing I in FIG. 5), and only the leak test of the work chamber is performed when a work is changed to another (during the timing II and III in FIG. 5). Alternatively, during the timing I in FIG. 5, the gas flow channel leak test and the supply unit leak test may be performed in parallel with each other instead of the collective leak test.

In the case where the gas leak check in the gas flow channel and that in the sterilizing substance supply unit 40 are performed in this way, heating of the heater 422 can be started in parallel with the gas flow channel leak test when the gas leak check in the sterilizing substance supply unit 40 is not performed, by reducing the number of the gas leak checks in the sterilizing substance supply unit 40. Therefore, the time necessary for the sterilizing process can be shortened. Alternatively, it may be designed that only the supply unit leak test is performed, for example, during the maintenance of the isolator 100. As stated above, the supply unit leak test can be set freely by providing the sterilizing substance supply unit 40 independently from the gas flow channel in terms of heat and pressure.

Collectively describing operational effects by the aforementioned structure, the isolator 100 according to the present embodiment comprises the sterilizing substance supply unit 40 that is provided independently from the gas flow channel, including the work chamber 10, in terms of heat and pressure, and heating of the heater 422 is performed in parallel with the gas flow channel leak test. Accordingly, the time necessary for the sterilizing process in the isolator 100 can be further shortened. As a result, the use efficiency of the isolator 100 is improved, thereby allowing for the production amount of a treated material to be increased.

In the isolator 100, the sterilizing substance supply unit 40 comprises the air supply fan 470 and the supply unit barometer 419, and is provided, by the valves 428 and 474, independently from the gas flow channel in terms of pressure. Accordingly, the supply unit leak test for checking a gas leak in the sterilizing substance supply unit 40 can be performed independently from the gas flow channel leak test. Thereby, the degree of freedom in setting the supply unit leak test is increased, and hence the usability of the isolator 100 can be further improved. Moreover, because the site where a gas leak has occurred can be easily specified by performing the supply unit leak test and the gas flow channel leak test independently from each other, the usability of the isolator 100 can be further improved.

Embodiment 2

Figure 6:
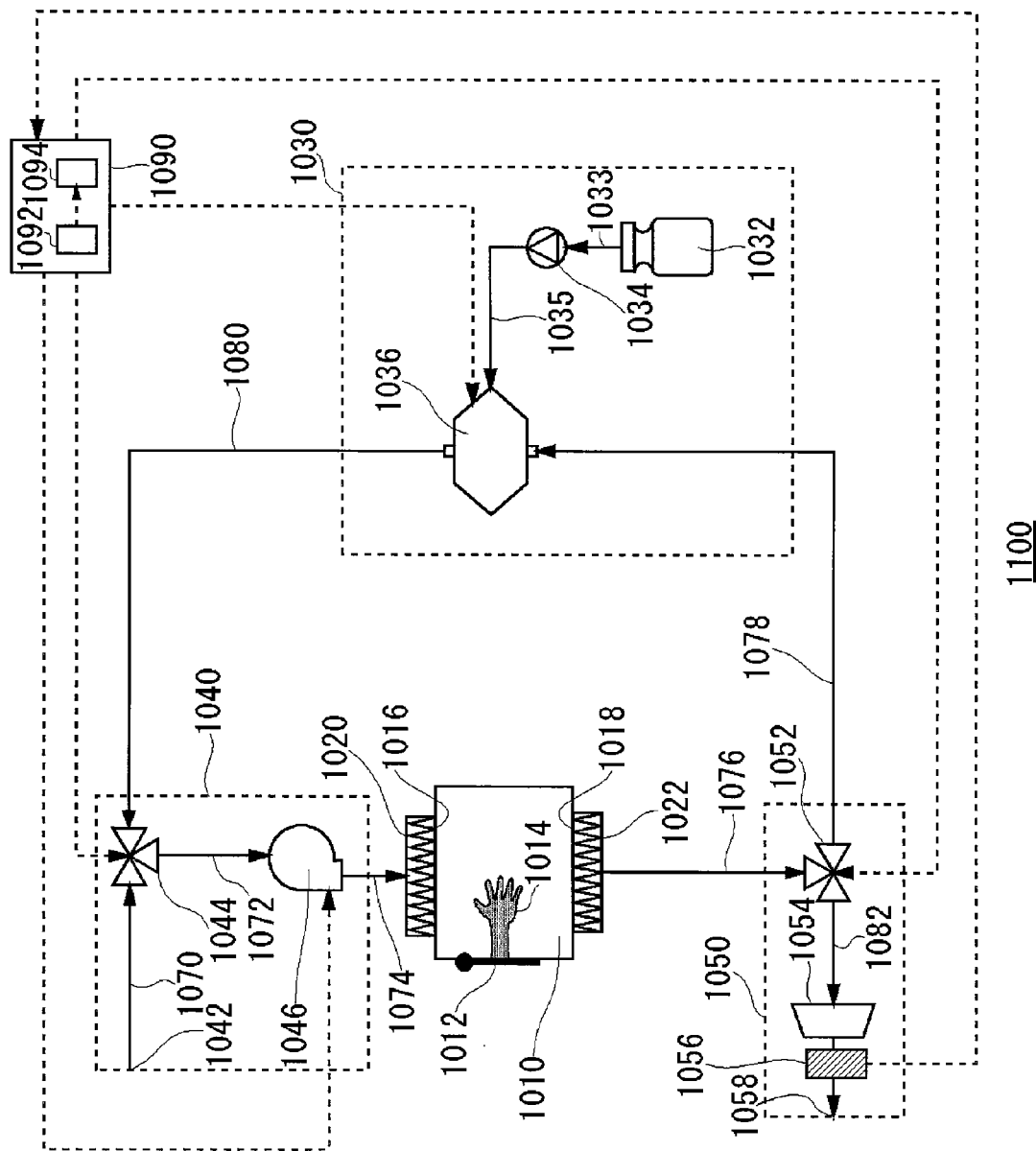
FIG. 6 is a schematic view illustrating the structure of an isolator according to Embodiment 2.

FIG. 6 is a schematic view illustrating the structure of an isolator 1100 according to Embodiment 2. The isolator 1100 according to Embodiment 1 comprises: a work chamber 1010 for performing a work in which a biomaterial is handled, such as cell extraction and cell culture; a gas supply unit 1040 configured to supply a gas into the work chamber 1010; a gas discharge unit configured to discharge the gas in the isolator 1100; a sterilizing substance supply unit 1030 configured to supply a sterilizing substance into the work chamber 1010; and a controller 1090 configured to control these operations. Herein, the biomaterial means a material that includes a living organism itself including cells, a substance of which a living organism is composed, or a substance that is produced by a living organism.

The gas supply unit 1040 is provided with an intake vent 1042, a three-way valve 1044, and a fan 1046. The open air is taken in through the intake vent 1042. The three-way valve 1044 is connected with the gas flow downstream side of the intake vent 1042 through a channel 1070 and connected with the gas flow downstream side of a sterilizing substance sending unit 1036 through a channel 1080. Further, the three-way valve 1044 is connected with the gas flow upstream side of the fan 1046 through a channel 1072. In the three-way valve 1044, the gas flow channel can be exclusively switched from the channel 1070 to the direction of the channel 1072 or from the channel 1080 to that of channel 1072. The air that is taken in through the intake vent 1042, or the gas that is sent through the channel 1080, which includes a sterilizing substance, is taken in by the fan 1046 through the three-way valve 1044.

The fan 1046 sends the gas, which has been taken in from the direction of the three-way valve 1044 through the channel 1072, in the direction of the work chamber 1010 through the channel 1074. ON/OFF switching of the fan 1046 can be controlled by the controller 1090. The discharge amount of the fan 1046 can be continuously controlled.

A front door 1012 is provided in the work chamber 1010 in an openable and closable manner, and work gloves 1014 for performing a work within the work chamber 1010 are provided at certain positions of the front door 1012. A worker can perform, through the work gloves 1014, a work within the work chamber 1010 after inserting his/her hands from not-illustrated openings that are provided on the front door 1012. The gas that has been sent by the fan 1046 is taken into the work chamber 1010 from the gas supply vent 1016 and the gas is discharged from a gas discharge vent 1018. HEPA filters 1020 and 1022 are provided in the gas supply vent 1016 and the gas discharge vent 1018, respectively. With these, the sterile state in the work chamber 1010 can be secured. The gas, which has been discharged from the work chamber 1010, is sent into a gas discharge unit 1050 through the gas discharge vent 1018, the HEPA filter 1022, and a channel 1076.

The gas discharge unit 1050 is provided with a three-way valve 1052, a sterilizing substance reduction process unit 1054, a concentration measurement unit 1056, and a discharge vent 1058 in this order according to the gas flow.

The three-way valve 1052 is connected with the gas flow downstream side of the work chamber 1010 through the channel 1076 and connected with the gas flow upstream side of the sterilizing substance reduction process unit 1054 through a channel 1082. Further, the three-way valve 1052 is connected with the gas flow upstream side of the sterilizing substance sending unit 1036 through a channel 1078. In the three-way valve 1052, the gas flow channel can be exclusively switched from the channel 1076 to the direction of the channel 1082 or from the channel 1076 to that of the channel 1078. The air, which has been taken in through the channel 1076, is sent in the direction of the channel 1082 or the channel 1078.

The sterilizing substance reduction process unit 1054 performs a reduction process for reducing the concentration of the sterilizing substance contained in the air, which has been sent through the three-way valve 1052. The sterilizing substance reduction process unit 1054 contains a metal catalyst, such as platinum, etc.; however, the process unit 1054 may contain activated carbon, etc.

The concentration measurement unit 1056 is provided in the gas flow downstream of the sterilizing substance reduction process unit 1054 such that the concentration of the sterilizing substance in the discharge gas, after the reduction process has been performed, is measured. A measurement result is transmitted from the concentration measurement unit 1056 to the controller 1090. The gas, which has been subjected to the reduction process by the sterilizing substance reduction process unit 1054, is discharged outside the isolator 1100 from the discharge vent 1058.

A sterilizing substance supply unit 1030 for supplying a sterilizing substance into the work chamber 1010 is provided outside the work chamber 1010. The sterilizing substance supply unit 1030 supplies a sterilizing substance into the work chamber 1010 to circulate the sterilizing substance within the isolator 1100 and thereby the work chamber 1010 and the channels can be made in a sterile environment. Herein, the sterile environment means an environment that is as close to a dust-free, sterile environment as possible to prevent contamination of substances other than ones necessary for the work to be performed in the work chamber. In the present embodiment, the sterilizing substance is hydrogen peroxide.

As illustrated in FIG. 6, the sterilizing substance supply unit 1030 is located on the gas flow downstream side of the three-way valve 1052 and the channel 1078, and located on the gas flow upstream side of the channel 1080 and the three-way valve 1044. The sterilizing substance supply unit 1030 has a sterilizing substance supply tank 1032, a pump 1034, and a sterilizing substance sending unit 1036. The sterilizing substance supply tank 1032 stores hydrogen peroxide solution as a sterilizing substance. The pump 1034 pumps the hydrogen peroxide solution, which is stored in the sterilizing substance supply tank 1032, through a sterilizing substance supply pipe 1033 and sends the hydrogen peroxide solution through a sterilizing substance supply pipe 1035. The sterilizing substance sending unit 1036 is connected with each of the gas flow downstream side of the three-way valve 1052 through the channel 1078 and the gas flow upstream side of the three-way valve 1044 through the channel 1080. The sterilizing substance sending unit 1036 generates hydrogen peroxide gas or mist from the supplied hydrogen peroxide solution. The generated hydrogen peroxide gas or mist is sent into the channel 1080.

Figure 7:
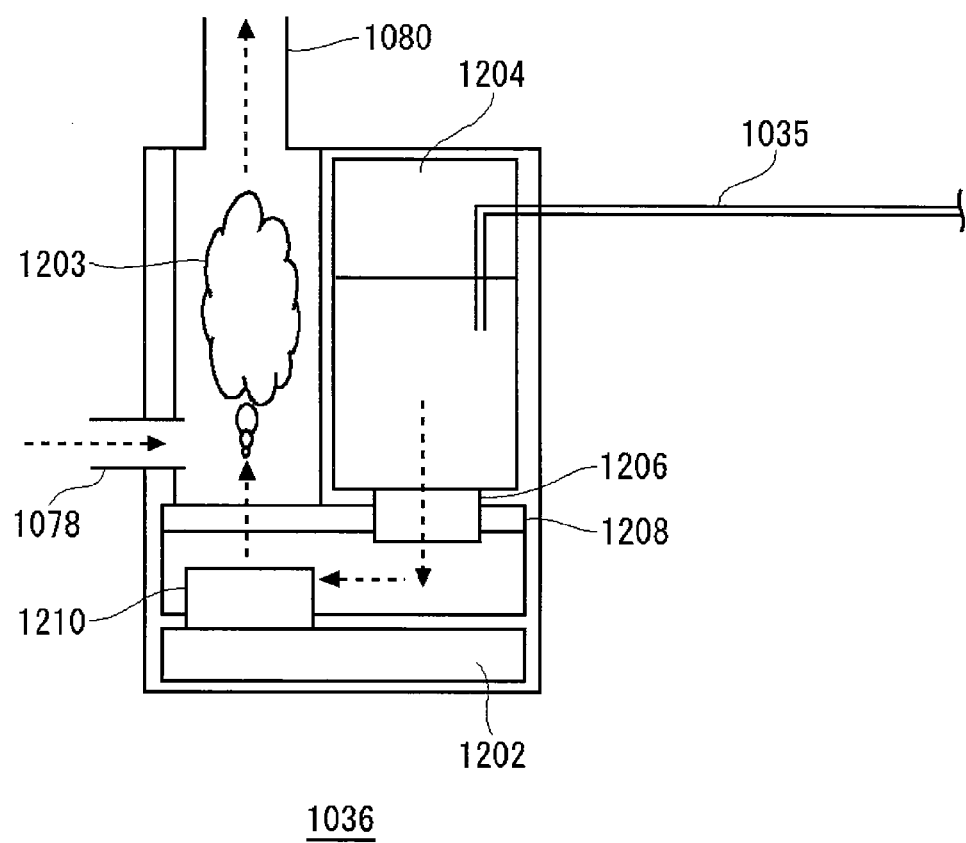
FIG. 7 is a schematic view illustrating a sterilizing substance sending unit.

FIG. 7 is a schematic view illustrating the sterilizing substance sending unit 1036. The specific structure of the sterilizing substance sending unit 1036 will be described with reference to the drawing. The sterilizing substance sending unit 1036 has a control substrate 1202, a hydrogen peroxide solution tank 1204, a water seal cap 1206, a hydrogen peroxide solution tub 1208, and an ultrasonic oscillator 1210.

The control substrate 1202 is a substrate for controlling the pump 1034. The hydrogen peroxide solution tank 1204 is a container for temporarily storing the hydrogen peroxide solution. The water seal cap 1206 is a cap for controlling the supply amount of the hydrogen peroxide solution, which is sent from the hydrogen peroxide solution tank 1204 to the hydrogen peroxide solution tub 1208. The hydrogen peroxide solution tub 1208, which is provided with the ultrasonic oscillator 1210 on its bottom, is a water tub for temporarily storing the hydrogen peroxide solution that has been sent from the hydrogen peroxide solution tank 1204. The ultrasonic oscillator 1210 is an oscillator for generating hydrogen peroxide gas or mist by ultrasonic oscillation. The hydrogen peroxide solution is housed in the sterilizing substance supply tank 1032 illustrated in FIG. 6, which is supplied, by the pump 1034 being controlled with, for example, the control substrate 1202, into the hydrogen peroxide solution tank 1204 from the sterilizing substance supply tank 1032 through the sterilizing substance supply pipes 1033 and 1035.

The hydrogen peroxide solution, which has been supplied into the hydrogen peroxide solution tank 1204, is supplied into the hydrogen peroxide solution tub 1208 through the water seal cap 1206 under the control of the control substrate 1202. The hydrogen peroxide gas (mist) 1203 is generated by providing ultrasonic oscillation using the ultrasonic oscillator 1210 to the hydrogen peroxide solution in the hydrogen peroxide solution tub 1208. Although the generated hydrogen peroxide gas (mist) 1203 is sent toward the work chamber 1010 through the channel 1080, most of the hydrogen peroxide gas rapidly vaporizes and is present in the work chamber 1010 as hydrogen peroxide gas or mist. Hereinafter, it is sometimes referred to as hydrogen peroxide gas including hydrogen peroxide mist.

Without limiting to the structure in which the hydrogen peroxide gas or mist is generated as in the present embodiment, the sterilizing substance sending unit 1036 may be a hydrogen peroxide gas generator, etc., in which hydrogen peroxide gas or mist is generated by, for example, hitting dropped hydrogen peroxide solution with air so as to vaporize the hydrogen peroxide solution. The sterilizing substance shall not be limited to hydrogen peroxide, but may be a substance containing, for example, an active oxygen species, such as ozone.

Referring back to FIG. 6, the controller 1090 will be described. The controller 1090 comprises a measurement unit 1092 and a recording unit 1094. The controller 1090 controls sending of the sterilizing substance by the sterilizing substance sending unit 1036. Further, the controller 1090 controls switching of the gas flow channel by controlling opening/closing of the three-way valve 1044 and 1052.

Specifically, the controller 1090 controls exclusive switching of the gas flow channel from the channel 1070 to the direction of the channel 1072 or from the channel 1080 to that of the channel 1072 by controlling opening/closing of the valve of the three-way valve 1044. Further, the controller 1090 controls exclusive switching of the gas flow channel from the channel 1076 to the direction of the channel 1082 or from the channel 1076 to that of the channel 1078 by controlling opening/closing of the valve of the three-way valve 1052. Further, the controller 1090 receives a measurement result from the concentration measurement unit 1056 and controls, based on the received measurement result, the rotational speed of the fan 1046 in accordance with a concentration measurement result of the hydrogen peroxide gas in the discharge air by the concentration measurement unit 1056, so that the discharge amount is continuously controlled. The measurement unit 1092 measures the time necessary from the start to the end of the sterilizing process. The recording unit 1094 records the measured time. The controller 1090 determines whether the performance of the sterilizing substance reduction process unit 1054 is deteriorated by using the measurement unit 1092 and the recording unit 1094.

(Switching of Gas Flow Channel)

The gas flow channel of the isolator 1100 is switched in the following two ways by the controller 1090 controlling opening/closing of the valves of the three-way valves 1044 and 1052. That is, when making the hydrogen peroxide gas circulate within the isolator 1100, the three-way valve 1044 is set such that only the direction from the channel 1080 toward the channel 1072 is in an open state and the direction from the channel 1070 toward the channel 1072 is in a closed state. The three-way valve 1052 is set such that only the direction from the channel 1076 toward the channel 1078 is in an open state and the direction from the channel 1076 toward the channel 1082 is in a closed state. Thereby, a circulation channel is formed in which: the hydrogen peroxide gas enters the work chamber 1010 from the sterilizing substance sending unit 1036 through the channel 1080, the three-way valve 1044, the channel 1072, the fan 1046, the channel 1074, the HEPA filter 1020, and the gas supply vent 1016; and returns to the sterilizing substance sending unit 1036 through the gas discharge vent 1018, the HEPA filter 1022, the channel 1076, the three-way valve 1052, and the channel 1078.

On the other hand, when substituting for the air in the work chamber, the three-way valve 1044 is set such that only the direction from the channel 1070 toward the channel 1072 is in an open state and the direction from the channel 1080 toward the channel 1072 is in a closed state. The three-way valve 1052 is set such that only the direction from the channel 1076 toward the channel 1082 is in an open state and the direction from the channel 1076 toward the channel 1078 is in a closed state. Thereby, a channel is formed in which: air enters the work chamber 1010 from the intake vent 1042 through the channel 1070, the three-way valve 1044, the channel 1072, the fan 1046, the channel 1074, the HEPA filter 1020, and the gas supply vent 1016; and the air is discharged from the discharge vent 1058 through the gas discharge vent 1018, the HEPA filter 1022, the channel 1076, the three-way valve 1052, the channel 1082, and the sterilizing substance reduction process unit 1054.

(Sterilizing Process)

In the isolator 1100, between the end of a work (previous work) within the work chamber 1010 and the start of the subsequent work, a sterilizing process for sterilizing the inside of the work chamber 1010 and the flow channels, which have been used in the previous work, is performed. The sterilizing process includes a pretreatment step, a sterilizing step, and a substitution step.

In the pretreatment step, hydrogen peroxide gas is supplied into the work chamber 1010 from the sterilizing substance supply unit 1030 such that the concentration of the hydrogen peroxide gas within the work chamber 1010 is maintained at a concentration, which is greater than or equal to the concentration necessary for the sterilization within the work chamber 1010. In the pretreatment step, when the concentration of the hydrogen peroxide gas within the work chamber 1010 becomes greater than or equal to a predetermined concentration, the sterilizing step is started.

In the sterilizing step, sterilization is performed by circulation of the hydrogen peroxide gas in which the hydrogen peroxide gas is sent into the work camber 1010 from the sterilizing substance supply unit 1030 and again returns to the sterilizing substance supply unit 1030 through the three-way valve 1052. More specifically, in the sterilizing step, the three-way valve 1044 is switched such that only the direction from the channel 1080 toward the channel 1072 is in an open state and the direction from the channel 1070 toward the channel 1072 is in a closed state. On the other hand, the three-way valve 1052 is switched such that only the direction from the channel 1076 toward the channel 1078 is in an open state and the direction from the channel 1076 toward the channel 1082 is in a closed state. Thereby, a gas flow channel is formed within the isolator 1100, in which the gas, which has been sent from the sterilizing substance sending unit 1036, enters the work chamber 1010 through the three-way valve 1044 and returns to the sterilizing substance sending unit 1036 through the three-way valve 1052, thus the hydrogen peroxide gas circulating within the isolator 1100.

In the substitution step, the air, which has been taken in through the intake vent 1042, is substituted for the gas within the work chamber 1010 by supplying the air into the work chamber 1010 to extrude the gas within the work chamber 1010. More specifically, in the substitution step, the controller 1090 switches the three-way valve 1044 such that only the direction from the intake vent 1042 toward the work chamber 1010 is in an open state, and switches the three-way valve 1052 such that only the direction from the work chamber 1010 toward the discharge vent 1058 is in an open state. Further, the controller 1090 turns on the fan 1046. Thereby, a gas flow channel is formed within the isolator 1100, in which the air that has been taken in from the intake vent 1042 is sent into the work chamber 1010 through the channel 1070 and the HEPA filter 1020 and is discharged from the discharge vent 1058 through the work chamber 1010 and the HEPA filter 1022. As a result, the air is substituted for the gas in the work chamber 1010 and the hydrogen peroxide gas within the work chamber 1010 is removed from the work chamber 1010.

In this case, the outflow of the hydrogen peroxide gas from the discharge vent 1058 to the outside of the isolator 1100 can be reduced by the hydrogen peroxide gas, which has been extruded from the work chamber 1010, being subjected to the reduction process by the sterilizing substance reduction process unit 1054. In this case, the controller 1090 controls the discharge amount from the fan 1046 based on a concentration measurement result by the concentration measurement unit 1056. Also, in the substitution step, the hydrogen peroxide gas, which remains within areas in the isolator 1100 other than the work chamber 1010, for example, the gas supply unit 1040, and the hydrogen peroxide that is adsorbed in the HEPA filters 1020 and 1022 in the flow channel, which have been used in the previous work, are removed.

In the substitution step, the subsequent work can be started when the concentration of the hydrogen peroxide gas within the work chamber 1010 is smaller than or equal to a predetermined concentration. The concentration of the hydrogen peroxide gas at which the subsequent work can be started means the concentration at which the biomaterial, which will be used in the subsequent work, is not affected to the extent that cannot be neglected for the work. The concentration is, for example, smaller than or equal to 1 ppm (TWA: Time Weighted Average) that is specified by ACGIH (American Conference of Government Industrial Hygienists). Alternatively, it may be possible that the time for which the concentration of the hydrogen peroxide gas within the work chamber 1010 becomes smaller than or equal to a predetermined concentration is experimentally determined and the subsequent work is to be started after the determined time has passed.

(Control of Discharge Amount in Substitution Step)

Figure 8:
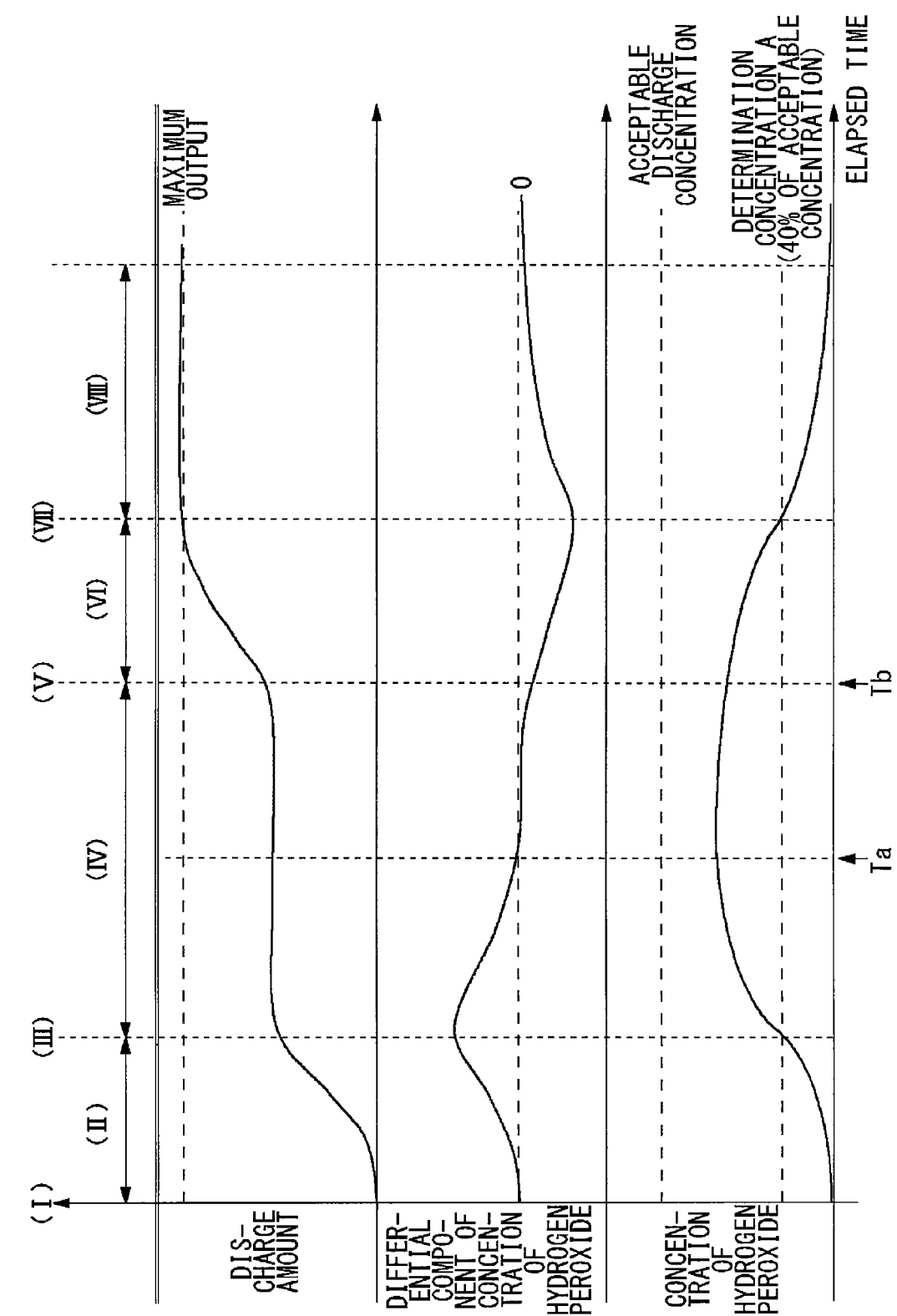
FIG. 8 is a schematic graph illustrating discharge control according to Embodiment 2.

Subsequently, changes in the concentration of the hydrogen peroxide gas and in the discharge amount in the substitution step will be described. FIG. 8 is a schematic graph illustrating the discharge control according to Embodiment 2. The upper curve, the middle curve, and the lower curve respectively illustrate the concentration of the hydrogen peroxide gas, the differential component as the rate of change in the concentration, and the successive change in the discharge amount in the substitution step in the isolator 1100 according to Embodiment 2.

As illustrated by the lower curve in FIG. 8, the concentration of the hydrogen peroxide gas is measured by the concentration measurement unit 1056, which is provided on the gas flow downstream side of the sterilizing substance reduction process unit 1054. The discharge amount from the gas discharge unit 1050 is controlled by increasing/reducing the rotational speed of the fan 1046 in accordance with an order from the controller 1090 based on the aforementioned measured concentration, namely, is controlled in the following way such that the acceptable discharge concentration does not exceed a predetermined threshold value. After the start of the discharge (I), the discharge amount is gradually increased by increasing the rotational speed of the fan 1046. Subsequently, after the concentration of the hydrogen peroxide gas in the discharge gas has reached a predetermined determination concentration A (III), the rotational speed of the fan 1046 is maintained within a predetermined range, thereby the discharge amount is maintained within a predetermined range, as illustrated by the upper curve in FIG. 8 (IV). As illustrated by the lower curve in FIG. 8, after the concentration of the hydrogen peroxide gas in the discharge gas has reached the maximum at the time Ta, the discharge is further continued. As illustrated by the middle curve in FIG. 8, after it is confirmed that the differential component (reduction rate) of the concentration of the hydrogen peroxide gas has exceeded a predetermined threshold value (V) at the time Tb, the discharge amount is gradually increased by again increasing the rotational speed of the fan 1046, as illustrated by the upper curve in FIG. 8 (VI). Further, as illustrated by the lower curve in FIG. 8, after the concentration of the hydrogen peroxide gas in the discharge gas has been reduced to the predetermined determination concentration A (VII), the discharge is continued at the maximum discharge amount until the discharge ends, as illustrated by the upper curve in FIG. 8 (VIII). The acceptable discharge concentration may be experimentally determined. It is desirable that the predetermined determination concentration A is approximately 40% of the acceptable discharge concentration, but may be experimentally determined. The differential component of the reduction rate in the concentration of the hydrogen peroxide gas is usually set to a certain negative value as the threshold value, but may be experimentally determined without being limited thereto. Herein, when the discharge amount has reached the maximum output as illustrated by the upper curve in FIG. 8, and when the concentration of the hydrogen peroxide gas cannot be measured because the concentration thereof is below the detection limit of the concentration measurement unit as illustrated by the lower curve in FIG. 8, the discharge is ended by reducing the rotational speed of the fan 1046 with the controller 1090. After the concentration thereof has reached the aforementioned detection limit, the discharge may be ended further after X/Y×5 to X/Y×10 sec (where X (m$^3$) is the volume of the work chamber 1010 and Y (m$^3$/sec) is the discharge capability of the fan 1046), namely, further after the time for which the gas within the work chamber 1010 is replaced 5 to 10 times has passed.

(Dealing with Performance Deterioration of Sterilizing Substance Reduction Process Unit)

Figure 9:
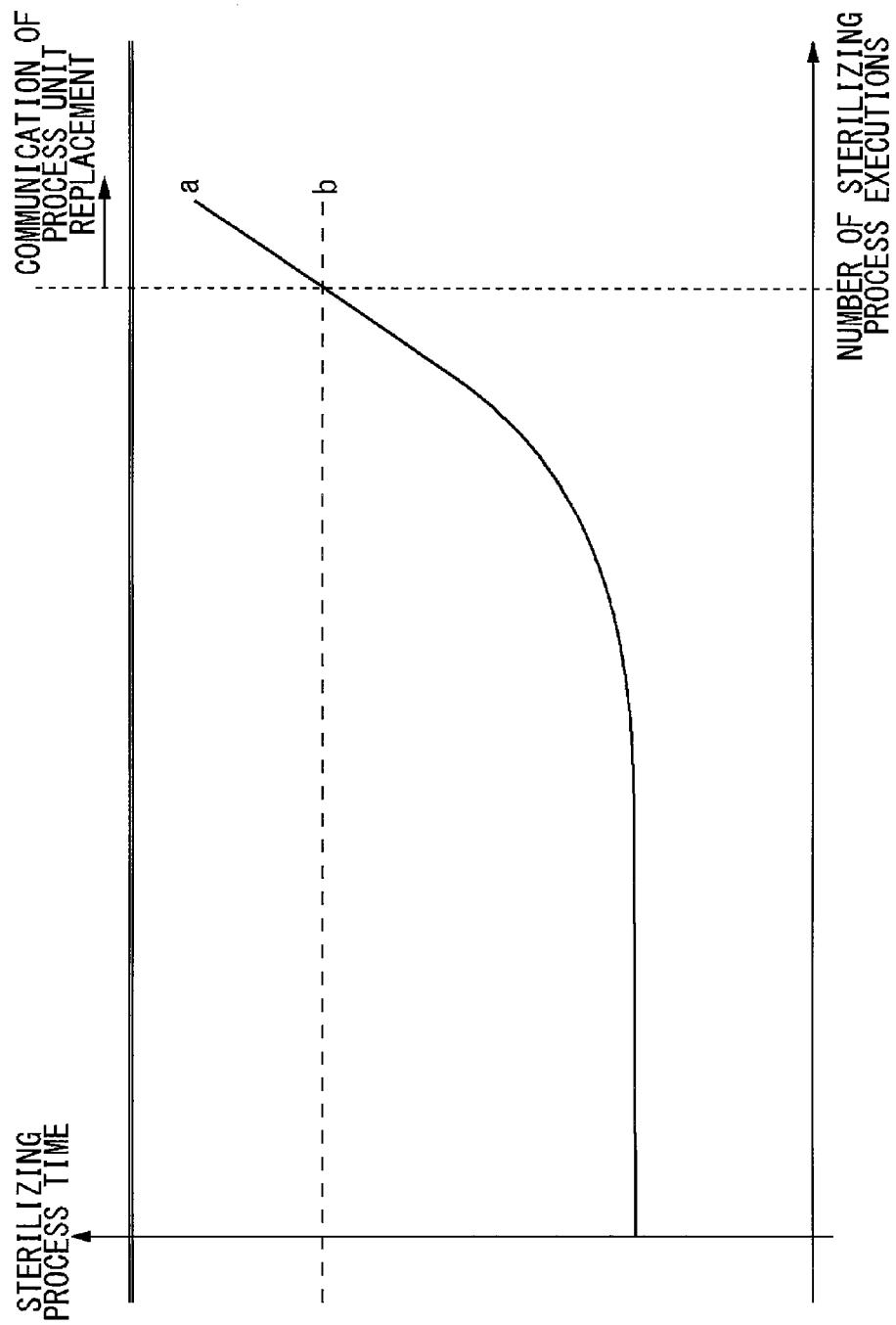
FIG. 9 is a schematic graph illustrating capability determination of a sterilizing substance reduction process unit according to Embodiment 2.

FIG. 9 is a schematic graph illustrating the relationship between the number of the sterilizing process executions and the sterilizing process time, and illustrating the capability determination of the sterilizing substance reduction process unit 1054 according to Embodiment 2.

The measuring unit 1092 measures the time (process time) between the start and the end of the sterilizing process, that is, the time for which a certain time has passed after the concentration of the hydrogen peroxide gas has reached the detection limit of the concentration measurement unit 1056. The recording unit 1094 records the measurement result in association with the number of the sterilizing process executions. The graph (a) in FIG. 9 is made by plotting each sterilizing process time (vertical axis), which is obtained herein, relative to the number of the sterilizing process executions (horizontal axis). Herein, the controller 1090 determines whether the process time, which has been measured by the measurement unit 1092 and recorded by the recording unit 1094, exceeds a predetermined threshold value (b). When the process time exceeds the threshold value, the controller 1090 communicates that the performance of the sterilizing substance reduction process unit 1054 has been deteriorated. Thereby, the process unit can be replaced at an appropriate time, and hence the concentration of the hydrogen peroxide gas can be reduced by using the sterilizing substance reduction process unit 1054, the performance of which is always greater than or equal to a predetermined level. The threshold value (b) of the time necessary for the sterilizing process may be experimentally determined. In addition, the equipment for automatically replacing the sterilizing substance reduction process unit 1054, the performance of which has been deteriorated, may be further provided, not only communicating that the performance of the sterilizing substance reduction process unit 1054 has been deteriorated.

In a conventional isolator, the concentration of the hydrogen peroxide gas within a work chamber is rapidly decreased immediately after the start of a substitution step; however, a reduction rate of the concentration thereof is significantly decreased. This is because efficient discharge cannot be performed in the second half of the substitution step in which the concentration of the hydrogen peroxide gas within the isolator becomes is low, since the discharge is performed at a constant discharge amount. Accordingly, the substitution step takes a long time as a result, thereby taking a long time before the work chamber is in a state if being able to be used. On the other hand, in the isolator 1100 according to Embodiment 2, which is illustrated in FIG. 6, the discharge amount is gradually increased in the substitution step, and after the concentration of the hydrogen peroxide gas within the work chamber 1010 has reached a predetermined concentration, the discharge amount is maintained within a predetermined range, in the substitution step. And, after it is confirmed that the reduction rate of the concentration of the hydrogen peroxide has reached a predetermined threshold value, the discharge amount is again gradually increased. Thereby, because the discharge of the hydrogen peroxide into the air, the hydrogen peroxide not being degraded, can be suppressed to the minimum in the first half of the substitution step, the safety of a worker can be secured and efficient discharge can be performed. Further, in the second half of the substitution step, the discharge can be efficiently performed when the concentration of the hydrogen peroxide gas that is being discharged is low because of the control of the discharge amount according to the present embodiment, although, in a conventional isolator, the discharge cannot be efficiently performed because the hydrogen peroxide gas is discharged at a constant discharge amount. Because of the control of the discharge amount, the time necessary for the substitution step can be shortened when performing a sterilizing process between the previous work and the subsequent work and the isolator 1100 can be set to the state in an earlier time where the subsequent work can be started.

Further, the aforementioned safety from the discharge gas can be more surely secured and the sterilizing time can be more surely shortened by communicating that the performance of the sterilizing substance reduction process unit 1054 has been deteriorated based on the measurement result by the measurement unit 1092.

Embodiment 3

Embodiment 3 is different from Embodiment 2 in the point that the discharge amount is controlled by feedback. Because the structure of the isolator 1100 other than that and the operations in the sterilizing process, etc., are the same as in Embodiment 2, the descriptions will be made with reference to like drawings and be appropriately omitted.

Figure 10:
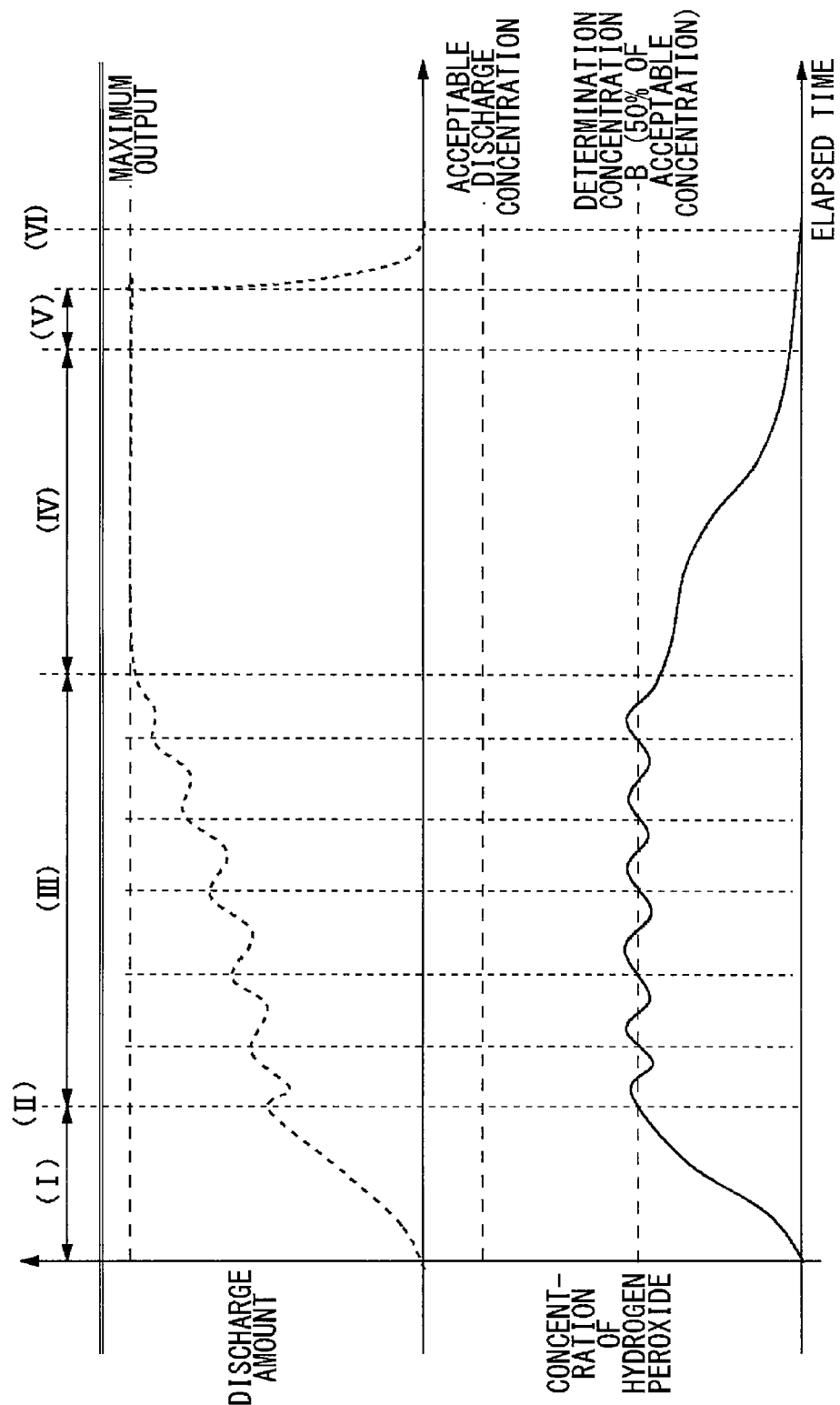
FIG. 10 is a schematic graph illustrating discharge control according to Embodiment 3.

FIG. 10 is a schematic graph illustrating discharge control according to Embodiment 3. Specifically, in the substitution step, in which feedback is performed, in the isolator 100, the successive changes in the concentration of the hydrogen peroxide gas and the discharge amount are illustrated.

The concentration of the hydrogen peroxide gas is measured by the concentration measurement unit 1056, which is provided on the gas flow downstream side of the gas discharge unit 1050 (see the lower curve in FIG. 10). The discharge amount of the gas discharge unit 1050 is controlled by increasing/reducing the rotational speed of the fan 1046 in accordance with an order from the controller 1090 based on the measurement result.

As illustrated by the upper curve in FIG. 10, the discharge amount is at first gradually increased by increasing the rotational speed of the fan 1046 after the start of the discharge (I). Subsequently, as illustrated by the lower curve in FIG. 10, the discharge amount is controlled by feedback by increasing/reducing the rotational speed after the concentration of the hydrogen peroxide gas has reached a predetermined determination concentration B (II). Herein, as illustrated by the upper curve in FIG. 10, the discharge amount is controlled by increasing/reducing the rotational speed of the fan 1046 in accordance with up/down of the concentration of the hydrogen peroxide gas, which has been measured by the concentration measurement unit 1056 (III).

That is, when the concentration of the hydrogen peroxide gas exceeds the predetermined determination concentration B, the rotational sped of the fan 1046 is reduced such that the discharge amount is reduced. On the other hand, when the concentration thereof becomes below the predetermined determination concentration B, the rotational speed of the fan 1046 is increased such that the discharge amount is increased. Thereby, the concentration of the hydrogen peroxide gas in the discharge gas is maintained within a predetermined range as illustrated by the lower curve in FIG. 10. Hereinafter, as illustrated by the upper curve in FIG. 10, the discharge amount is gradually increased while the discharge amount is slightly being increased/reduced such that the discharge amount is set to the maximum output, which is maintained (IV). As illustrated by the upper curve in FIG. 10, after the concentration thereof has reached the detection limit of the concentration measurement unit 1056, the discharge is further continued at the maximum discharge amount (V), and then the discharge is ended (VI). It is desirable that the predetermined determination concentration B is approximately 50% of the acceptable discharge concentration, but may be experimentally determined. In addition, the determination concentration B is not a certain value but a certain range in which the upper limit and the lower limit are specified. In this case, the discharge amount may be controlled so as to be increased when the concentration of the hydrogen peroxide gas in the discharge gas exceeds the upper limit value and to be reduced when the concentration thereof becomes below the lower limit value. In the present embodiment, similar effects as in Embodiment 2 can be obtained.

Embodiment 4

Embodiment 4 is different from Embodiment 2 in the point that another concentration measurement unit 1060 (see FIG. 11), which is used for measuring the concentration of the hydrogen peroxide gas, is further provided on the gas flow upstream side of the sterilizing substance reduction process unit 1054. Because the structure of the isolator 1300 other than that and the operations for the sterilizing process are the same as those in Embodiments 2 and 3, descriptions will be made by using like symbols and be appropriately omitted.

Figure 11:
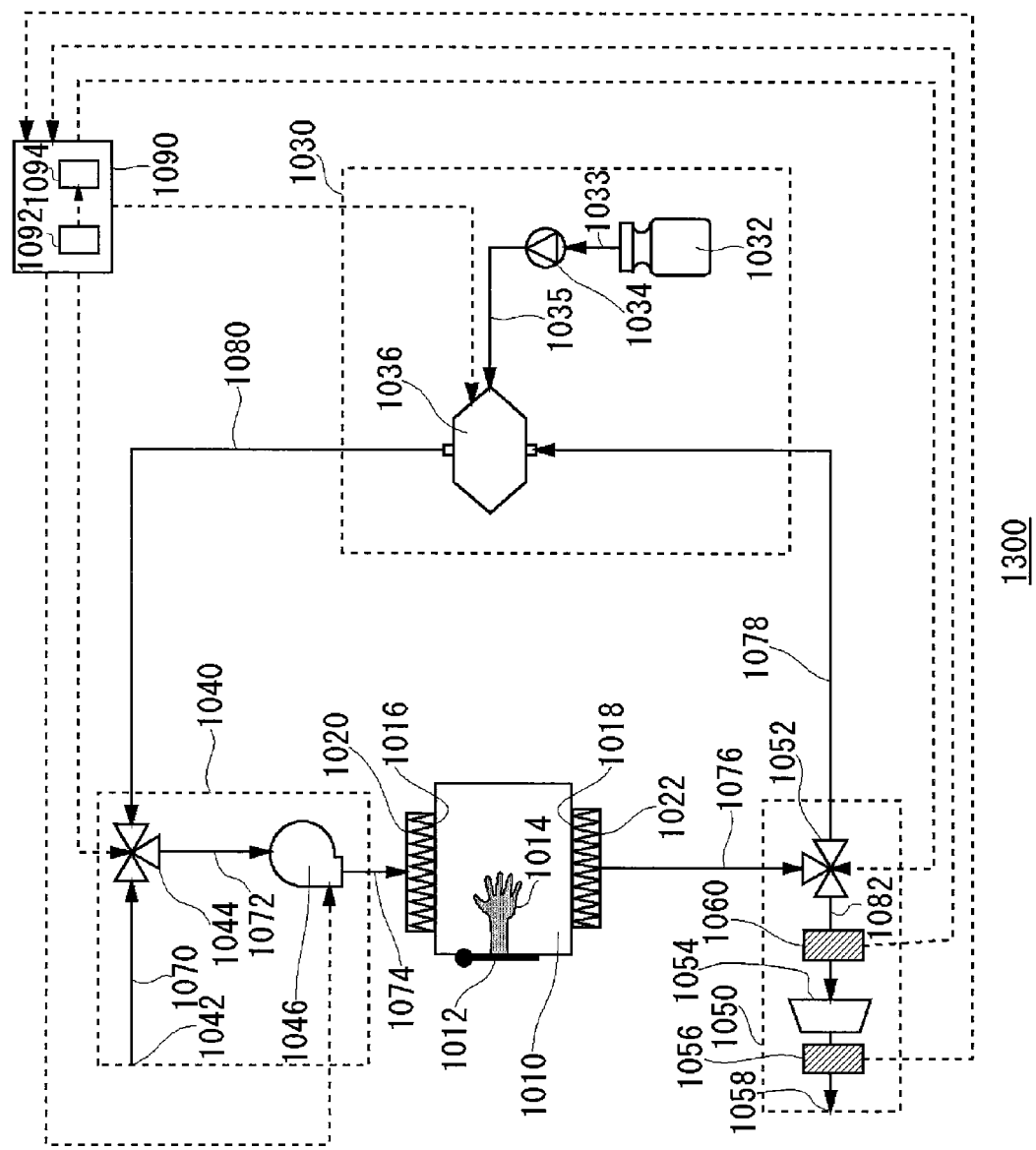
FIG. 11 is a schematic view illustrating the structure of an isolator according to Embodiment 4.
Figure 12:
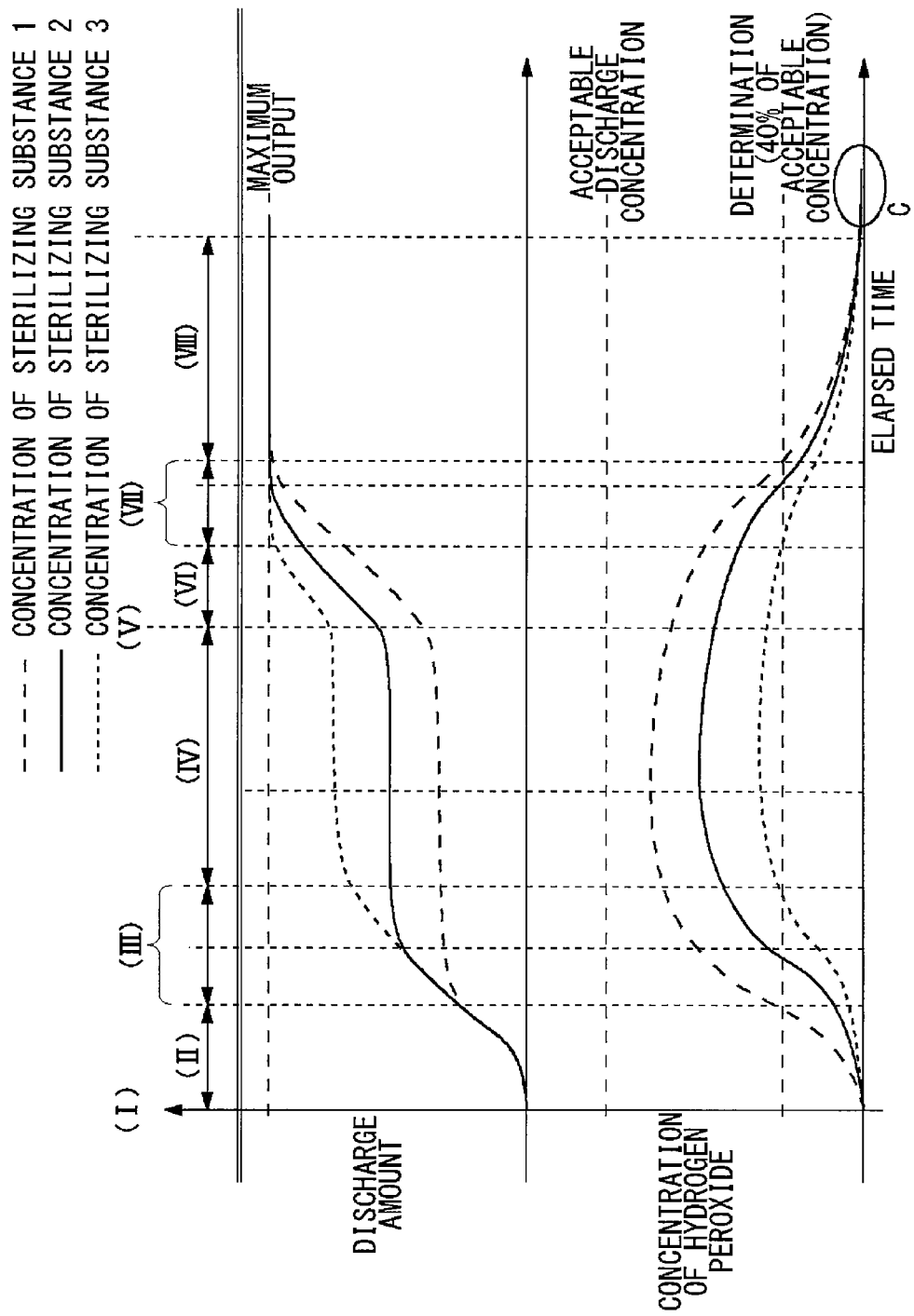
FIG. 12 is a schematic graph illustrating discharge control according to Embodiment 4.
Figure 13:
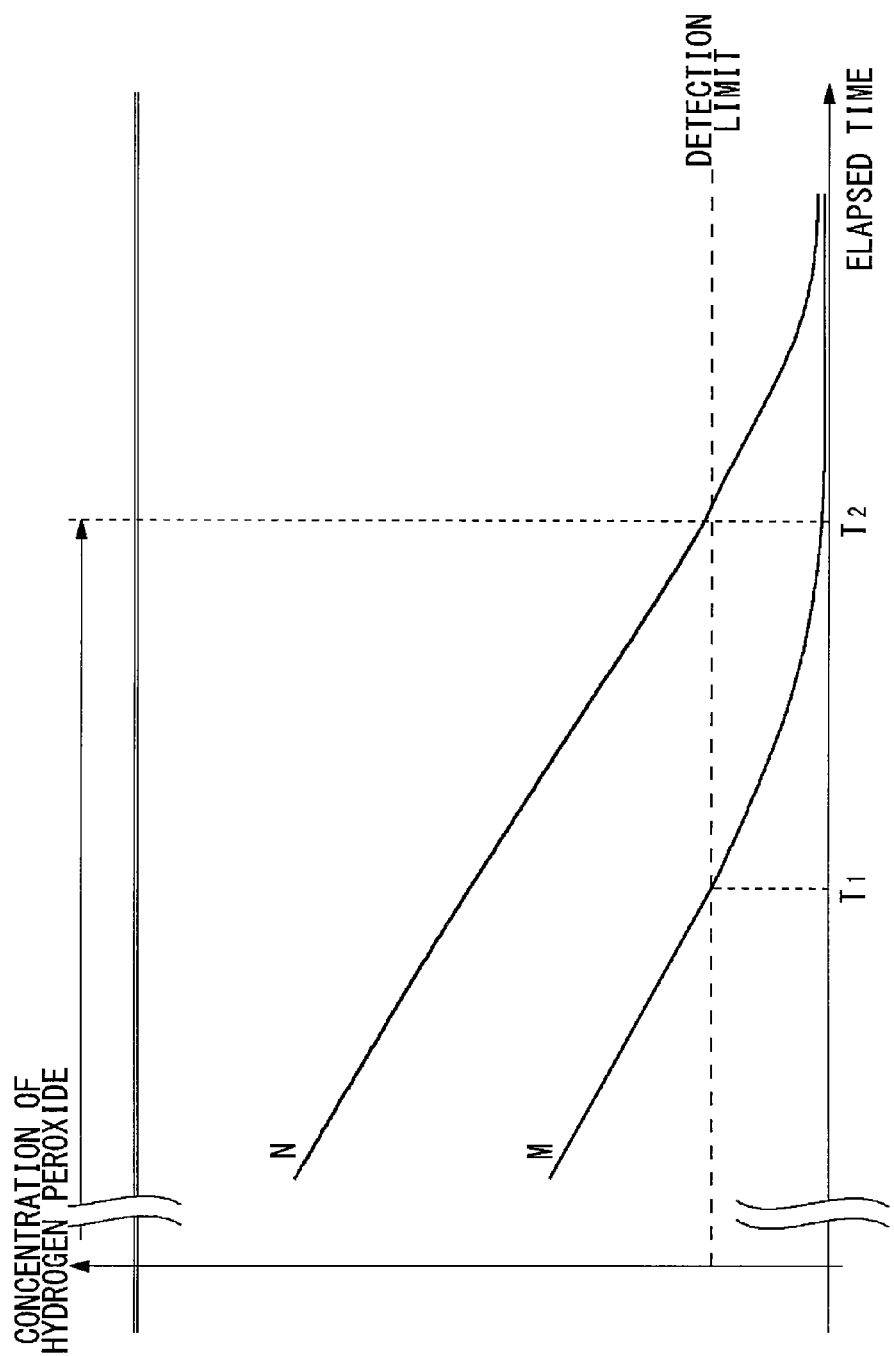
FIG. 13 is a schematic graph in which the detection limit region C of the concentration of the hydrogen peroxide gas in FIG. 12 is enlarged.

FIG. 11 is a schematic view illustrating the structure of an isolator according to Embodiment 4. FIG. 12 is a schematic graph illustrating discharge control according to Embodiment 4, that is, successive changes in the concentration of the hydrogen peroxide gas and in the discharge amount in the substitution step. In FIG. 12, three patterns of the concentration I (high concentration), the concentration II (middle concentration), and the concentration III (low concentration) have been illustrated. FIG. 13 is a schematic graph in which the detection limit region C of the concentration of the hydrogen peroxide gas in FIG. 12 is enlarged. M illustrates the successive change in the concentration of the hydrogen peroxide gas, which has been measured by using the concentration measurement unit 1056 on the gas flow downstream side of the sterilizing substance reduction process unit 1054. On the other hand, N illustrates the successive change in the concentration of the hydrogen peroxide gas, which has been measured by another concentration measurement unit 1060 provided on the gas flow upstream side of the sterilizing substance reduction process unit 1054.

As illustrated in FIG. 13, after the measured value (M) by the concentration measurement unit 1056, which is provided on the gas flow downstream side of the sterilizing substance reduction process unit 1054, has reached the detection limit at the time T1, the concentration thereof is continuously measured by using the concentration measurement unit 1060, which is provided on the gas flow upstream side of the sterilizing substance reduction process unit 1054, before the measured value by the concentration measurement unit 1060 reaches the detection limit at the time T2, thereafter ending the discharge. By measuring, based on a measurement result by the concentration measurement unit 1060, the concentration of the hydrogen peroxide gas on the gas flow downstream side of the sterilizing substance reduction process unit 1054 after a measured value has reached the detection limit of concentration measurement unit 1056, a similar effect as in the case where the detection limit of the concentration measurement unit 1056 is lowered can be obtained. Alternatively, only the concentration measurement unit 1060 may be provided without the concentration measurement unit 1056, which is provided on gas flow downstream side, being provided. In this case, the isolator 1100 may be controlled by the controller 1090 based on a measurement result by the concentration measurement unit 1060 so as to exhibit a similar effect as in Embodiments 2 and 3.

The present invention shall not be limited to any one of the aforementioned Embodiments 1 to 4, but various modifications such as design modification could be made based on the knowledge of a skilled person. Such modifications could be also within the scope of the present invention.

For example, the isolator 1100 according to each of the aforementioned embodiments may be provided with a non-illustrated heater for heating the HEPA filter 1020 as a heating means. According to the heater, the hydrogen peroxide, which is adsorbed in the HEPA filter 1020, can be peeled off more easily. In addition, when the hydrogen peroxide is adsorbed in the HEPA filter 1020 in a solution state, it can be prevented that heat is consumed as the vaporization heat when the hydrogen peroxide in a solution state is vaporized, and hence the temperature is decreased and the vaporization of the hydrogen peroxide is suppressed. It may be designed that ON/OFF of the heater and the heating amount are controlled by the controller. It is desirable that the heating amount for the HEPA filter 1020 by the heater is to the extent in which a change in the temperature in the work chamber 1010 can be suppressed to, for example, 5° C. or less. The heating of the HEPA filter 1020 by the heater is performed, for example, on the HEPA filter that has been used in the previous work after the gas flow channel has been switched to the flow channel, which has not been used in the previous work, in the substitution step.

Although, in the aforementioned Embodiments 2 through 4, the HEPA filters 1020 and 1022 are provided on the side surface of the work chamber 1010, these filters may be provided at positions remote from the work chamber 1010.

In the aforementioned Embodiments 2 through 4, the fan 1046, which is an intake fan, is only used and the fan is designed to have the function as a discharge fan as well. However, the fan shall not be limited to an intake fan, but may be a discharge fan. Alternatively, both an intake fan and a discharge fan may be provided. In the latter case, the discharge amount of the intake fan may be controlled by the controller 1090 such that the discharge amount thereof is almost the same as that of the discharge fan.

Although, in the aforementioned Embodiments 2 through 4, a pass box, a three-way valve for controlling the air in the pass box, and a fan are not provided, an isolator that is provided with these components may be possible. Herein, the pass box means the equipment that is provided on the wall surface of a work chamber and by which entrance and exit of dust, etc., can be prevented when tools or goods are transferred between an anterior chamber and a work chamber, thereby entrance of dust into the work chamber can be suppressed to the minimum.

In the aforementioned Embodiments 2 through 4, a plurality of valves may be used such that flow channels can be switched or a three-way valve may not be used, as long as similar effects as in these Embodiments can be exhibited.

What is claimed is:

1. An isolator comprising:
   a work chamber for performing a work in which a biomaterial is handled;
   a sterilizing substance supply unit that is provided in a state independent from a gas flow channel including the work chamber in terms of heat and pressure, and that has a heater for heating a sterilizing substance to be vaporized, and that is configured to supply the vaporized sterilizing substance into the gas flow channel;
   a gas flow channel pressure adjustment unit configured to increase or decrease the pressure in the gas flow channel;
   a gas flow channel pressure detector configured to detect the pressure inside the gas flow channel; and
   a controller configured to control execution of a gas flow channel leak test for checking a gas leak in the gas flow channel based on a detection result by the gas flow channel pressure detector after making the gas flow channel pressure adjustment unit increase or decrease the pressure in the gas flow channel, and configured to perform heating of the heater in parallel with the execution of the gas flow channel leak test,
   wherein a heat insulating portion which insulates heat and a shield which insulates pressure are provided between the gas flow channel and the sterilizing substance supply unit.

2. The isolator according to claim 1 comprising:
   a supply unit pressure adjustment unit configured to increase or decrease the pressure in the sterilizing substance supply unit; and
   a supply unit pressure detector configured to detect the pressure in the sterilizing substance supply unit, wherein the controller makes the supply unit pressure adjustment unit increase or decrease the pressure in the sterilizing substance supply unit when the heater is at normal temperature, and the controller controls execution of a supply unit leak test for checking a gas leak in the sterilizing substance supply unit based on a detection result by the supply unit pressure detector.

3. The isolator according to claim 1, wherein the controller is configured to control the supply of the sterilizing substance by the sterilizing substance supply unit.

4. The isolator according to claim 3, wherein the heat insulating portion is made from resin and the shield is a valve.

5. The isolator according to claim 1, wherein the controller is configured to compare the pressure inside the gas flow channel to a predetermined pressure value.

6. The isolator according to claim 5, wherein a gas leak is detected when the pressure inside the gas flow channel is determined to be less than the predetermined pressure value when the gas flow channel leak test is conducted in a state of positive pressure.

7. The isolator according to claim 6, wherein a gas leak is detected when the pressure inside the gas flow channel is determined to be greater than the predetermined pressure value when the gas flow channel leak test is conducted in a state of negative pressure.

8. An isolator comprising:
   a work chamber for performing a work in which a biomaterial is handled;
   a gas supply unit configured to supply a gas into the work chamber;
   a gas discharge unit configured to discharge the gas from the work chamber;
   a connection channel that has a particulate trap filter and connects the gas supply unit with the work chamber;
   a sterilizing substance supply unit configured to supply a sterilizing substance into the work chamber;
   a concentration measurement unit for measuring the concentration of the sterilizing substance discharged from the work chamber;
   a discharge means configured to control the discharge amount of the gas that is discharged from the das discharge unit;
   a reduction process unit configured to reduce the concentration of the sterilizing substance that is contained in the gas discharged from the gas discharge unit; and
   a controller configured to receive measurements from the concentration measurement unit and based on the measurements to control the discharge means to make the discharge amount at the end of the discharge larger than that occurring when the concentration of the sterilizing substance reaches the maximum after sterilizing the inside of the work chamber by supplying the sterilizing substance into the work chamber to maintain the concentration of the sterilizing substance in the work chamber.

9. The isolator according to claim 8 further comprising:
   a concentration measurement unit that is provided in the gas discharge unit and configured to measure the concentration of the sterilizing substance remaining in the gas that is discharged from the gas discharge unit, wherein the controller gradually increases the discharge amount before the concentration, which has been measured by the concentration measurement unit, reaches a predetermined determination concentration and the controller maintains the discharge amount within a predetermined range after the concentration has reached the determination concentration, and the controller further gradually increases the discharge amount on condition that a reduction rate of the concentration, which has been measured by the concentration measurement unit, exceeds a predetermined threshold value.

10. The isolator according to claim 9 further comprising:
    another concentration measurement unit, which is provided on the gas flow upstream side of the reduction process unit, when the concentration measurement unit is provided on the gas flow downstream side of the reduction process unit, wherein the controller measures, by using the another measurement unit, the concentration of the sterilizing substance in the discharge gas before being subjected to the reduction process on condition that the concentration of the sterilizing substance in the discharge gas after being subjected to the reduction process has reached the detection limit of the concentration measurement unit, the concentration being measured by the concentration measurement unit, and the controller ends the discharge by the gas discharge unit on condition that the concentration of the sterilizing substance, which has been measured by the another concentration measurement unit, has reached the detection limit of the another concentration measurement unit.

11. The isolator according to claim 10 comprising:
a measurement unit configured to measure the time elapsed since the discharge of the gas in the work chamber is started until the concentration of the sterilizing substance reaches the detection limit of the concentration measurement unit, wherein the controller communicates that the capability of the reduction process unit is decreased when the measured time exceeds a predetermined threshold value.

12. The isolator according to claim 11, wherein the sterilizing substance is hydrogen peroxide.

13. The isolator according to claim 10, wherein the sterilizing substance is hydrogen peroxide.

14. The isolator according to claim 9 comprising:
a measurement unit configured to measure the time elapsed since the discharge of the gas in the work chamber is started until the concentration of the sterilizing substance reaches the detection limit of the concentration measurement unit, wherein the controller communicates that the capability of the reduction process unit is decreased when the measured time exceeds a predetermined threshold value.

15. The isolator according to claim 14, wherein the sterilizing substance is hydrogen peroxide.

16. The isolator according to claim 9, wherein the sterilizing substance is hydrogen peroxide.

17. The isolator according to claim 8 further comprising:
a concentration measurement unit that is provided in the gas discharge unit and configured to measure the concentration of the sterilizing substance remaining in the gas that is discharged from the gas discharge unit, wherein the controller controls the discharge amount by feedback using the concentration, which has been measured by the concentration measurement unit, so that the discharge amount is gradually increased before the concentration reaches a predetermined determination concentration and that the concentration of the sterilizing substance in the discharge gas is within a predetermined range after the concentration has reached the determination concentration, and the controller fixes the discharge amount on condition that the discharge amount has reached a predetermined discharge amount.

18. The isolator according to claim 17 further comprising: another concentration measurement unit, which is provided on the gas flow upstream side of the reduction process unit, when the concentration measurement unit is provided on the gas flow downstream side of the reduction process unit, wherein the controller measures, by using the another measurement unit, the concentration of the sterilizing substance in the discharge gas before being subjected to the reduction process on condition that the concentration of the sterilizing substance in the discharge gas after being subjected to the reduction process has reached the detection limit of the concentration measurement unit, the concentration being measured by the concentration measurement unit, and the controller ends the discharge by the gas discharge unit on condition that the concentration of the sterilizing substance, which has been measured by the another concentration measurement unit, has reached the detection limit of the another concentration measurement unit.

19. The isolator according to claim 18 comprising:
a measurement unit configured to measure the time elapsed since the discharge of the gas in the work chamber is started until the concentration of the sterilizing substance reaches the detection limit of the concentration measurement unit, wherein the controller communicates that the capability of the reduction process unit is decreased when the measured time exceeds a predetermined threshold value.

20. The isolator according to claim 19, wherein the sterilizing substance is hydrogen peroxide.

21. The isolator according to claim 18, wherein the sterilizing substance is hydrogen peroxide.

22. The isolator according to claim 17 comprising:
a measurement unit configured to measure the time elapsed since the discharge of the gas in the work chamber is started until the concentration of the sterilizing substance reaches the detection limit of the concentration measurement unit, wherein the controller communicates that the capability of the reduction process unit is decreased when the measured time exceeds a predetermined threshold value.

23. The isolator according to claim 22, wherein the sterilizing substance is hydrogen peroxide.

24. The isolator according to claim 17, wherein the sterilizing substance is hydrogen peroxide.

25. The isolator according to claim 8, wherein the sterilizing substance is hydrogen peroxide.

26. The isolator according to claim 8, the concentration measurement unit is configured to measure the concentration of the sterilizing substance passed through the reduction process unit.

27. An isolator comprising:
a work chamber for performing a work in which a biomaterial is handled;
a sterilizing substance supply unit that is provided in a state independent from a gas flow channel including the work chamber in terms of heat and pressure, and that has a heater for heating a sterilizing substance to be vaporized, and that is configured to supply the vaporized sterilizing substance into the gas flow channel;
a gas flow channel pressure adjustment unit configured to increase or decrease the pressure in the gas flow channel;
a gas flow channel pressure detector configured to detect the pressure inside the gas flow channel; and
a controller configured to control execution of a gas flow channel leak test for checking a gas leak in the gas flow channel based on a detection result by the gas flow channel pressure detector after making the gas flow channel pressure adjustment unit increase or decrease the pressure in the gas flow channel, and configured to perform heating of the heater in parallel with the execution of the gas flow channel leak test and to compare the pressure inside the gas flow channel to a predetermined pressure value,
wherein a gas leak is detected when the pressure inside the gas flow channel is determined to be greater than the predetermined pressure value when the gas flow channel leak test is conducted in a state of negative pressure.

* * * * *